US009416118B2

(12) United States Patent
Serhan et al.

(10) Patent No.: US 9,416,118 B2
(45) Date of Patent: Aug. 16, 2016

(54) DOCOSAHEXAENOYL ETHANOLAMIDES

(75) Inventors: Charles N. Serhan, Needham, MA (US); Rong Yang, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 14/124,761

(22) PCT Filed: Jun. 8, 2012

(86) PCT No.: PCT/US2012/041510
§ 371 (c)(1),
(2), (4) Date: Apr. 21, 2014

(87) PCT Pub. No.: WO2012/170791
PCT Pub. Date: Dec. 13, 2012

(65) Prior Publication Data
US 2015/0025257 A1    Jan. 22, 2015

Related U.S. Application Data

(60) Provisional application No. 61/495,705, filed on Jun. 10, 2011.

(51) Int. Cl.
| A61K 31/335 | (2006.01) |
| A61K 31/16 | (2006.01) |
| C07D 303/08 | (2006.01) |
| C07D 303/46 | (2006.01) |
| A61K 47/48 | (2006.01) |
| C07C 235/28 | (2006.01) |
| C07K 5/02 | (2006.01) |
| C07D 303/14 | (2006.01) |

(52) U.S. Cl.
CPC ........ *C07D 303/46* (2013.01); *A61K 47/48246* (2013.01); *C07C 235/28* (2013.01); *C07D 303/14* (2013.01); *C07K 5/0215* (2013.01)

(58) Field of Classification Search
CPC .. C07C 235/28; C07D 303/46; C07D 303/08; C07D 303/14; A61K 47/48246; C07K 5/0215
USPC ...................... 549/553; 554/66; 514/627, 475
See application file for complete search history.

(56) References Cited

U.S. PATENT DOCUMENTS 6,353,012 B1    3/2002  Hellberg et al.
8,273,792 B2 *  9/2012  Serhan et al. ................. 514/549
8,853,437 B2   10/2014  Arita et al.

FOREIGN PATENT DOCUMENTS

| EP | 2208720 A1 | 7/2010 |
| WO | WO 2006-055965 A2 | 5/2006 |
| WO | WO 2010-095706 A1 | 8/2010 |

OTHER PUBLICATIONS

Marcheselli et al, Neuroprotectin D1/Protectin D1 stereoselelctive and specific binding with human retinal pigment epithetial cells and neutrophils, Prostaglandins, Leukotrienes and Essential Fatty Acids, 2010, 82(1), p. 27-34.*

(Continued)

*Primary Examiner* — T. Victor Oh
(74) *Attorney, Agent, or Firm* — Christensen Fonder, P.A.; Colin L. Fairman

(57) ABSTRACT

The invention describes novel mono or dihydroxy docosahexaenoic acid (DHA) analogs, their preparation, isolation, identification, purification and uses thereof.

18 Claims, 10 Drawing Sheets

(56) References Cited

OTHER PUBLICATIONS

Rodriguez et al, First total synthesis of 7(s)-Resovin D5, a potent anti-inflammatory docosanoid, Tetrahedron Letters 46 ,2005, p. 3623-3627.*
Seal et al, Liquid chromatography coordination ion-spray mass spectrometry (LC-CIS-MS)of docosahexaenoate ester hydroperoxides, Anal. Bioanal. Chem. , 2004, 378: p. 1007-1013.*
Bazan, et al., "Rescue and repair during photoreceptor cell renewal mediated by docosahexaenoic acid-derived neuroprotection D1,", (2010) J Lipid Res, No. 51, 2010, pp. 2018-2031.
Berge, et al., "Pharmaceutical Salts," J. Pharm. Sci., vol. 66, No. 1, 1977, pp. 1-19.
Berger, et al., "Anandamide and diet: inclusion of dietary arachidonate and docosahexaenoate leads to increased brain levels of the corresponding N-acylethanolamines in piglets", Proc Natl Acad Sci USA, No. 98, 2010, pp. 6402-6406.
Brown, et al., "Cannabinoid receptor-dependent and -independent anti-proliferative effects of omega-3 ethanolamines in androgen receptor-positive and -negative prostate cancer cell lines", Carcinogenesis, vol. 31, No. 9, 2010, pp. 1584-1591.
Calder, "Satellite Symposium: Throw another fish on the fire: the role of n-3 in inflammation Rationale and use of n-3 fatty acids in artificial nutrition", Proceedings of the Nutrition Society, vol. 69. Issue No. 4, Nov. 2010, pp. 565-573.
Dona, et al., "Resolvin E1, an EPA-derived mediator in whole blood, selectively counterregulates leukocytes and platelets" Blood 112(3), 848-855.
Felder, et al., "Anandamide, an endogenous cannabimimetic elcosanoid, binds to the cloned human cannabinoid receptor and stimulates receptor-mediated signal transduction", Proc Natl Acad Sci U S A 90(16), 1993, pp. 7656-7660.
Franklin, et al., "Palmitoylethanolamide increases after focal cerebral ischemia and potentiates microglial cell motility", J Neurosci 23(21), 2003, pp. 7767-7775.
Furman, et al. "Circulating monocyte-platelet aggregates are an early marker of acute myocardial infarction", J Am Coll Cardiol 38(4), 2001, pp. 1002-1006.
Hassan, et al., "Acute changes in dietary omega-3 and omega-6 polyunsaturated fatty acids have a pronounced impact on survival following ischemic renal injury and formation of renoprotective docosahexaenoic acid-derived protectin D1", J Immunol 182, 2009, pp. 3223-3232.
International Search Report and Written Opinion from related International Application No. PCT/US2012/041510, dated Feb. 21, 2013, 11 pages.
International Preliminary Report on Patentability from related International Application No. PCT/US2012/041510, dated Dec. 10, 2013, 6 pages.
Irimia, et al., "Microfluidic system for measuring neutrophil migratory responses to fast switches of chemical gradients", Lab Chip 6(2), 2006, pp. 191-198.
Kasuga, et al., "Rapid Appearance of Resolvin Precursors in Inflammatory Exudates: Novel Mechanisms in Resolution", J Immunol 181, 2008, pp. 8677-8687.
Kim, et al., "N-Docosahexaenoylethanolamide promotes development of hippocampal neurons", Biochem. J. vol. 435, No. 2, 2011, pp. 327-336, doi:10.1042/BJ20102118.
Krishnamoorthy, et al., "Resolvin D1 binds human phagocytes with evidence for proresolving receptors", Proc Natl Acad Sci USA 107, 2010, pp. 1660-1665.
Marcheselli, et al., "Novel docosanoids inhibit brain ischemia-reperfusion-mediated leukocyte infiltration and pro-inflammatory gene expression", J Biol Chem 278, 2003, pp. 43807-43817.
Nishiura, et al., "Monocyte chemotactic factor in rheumatoid arthritis synovial tissue. Probably a cross-linked derivative of S19 ribosomal protein", J Biol Chem 271(2), 1996, pp. 878-882.

Olson, et al., "Beta galactosidase complementation: a cell-based luminescent assay platform for drug discovery", Assay Drug Dev Technol 5(1), 2007, pp. 137-144.
Qui, et al., "IMP and AMP deaminase in reperfusion injury down-regulates neutrophil recruitment", Proc Natl Acad Sci USA 97, 2000, pp. 4267-4272.
Rinder, et al., "Dynamics of leukocyte-platelet adhesion in whole blood", Blood 78(7), 1991, pp. 1730-1737.
Sarma, et al., "Increased platelet binding to circulating monocytes in acute coronary syndromes", Circulation 105(18), 2002, pp. 2166-2171.
Serhan, et al., "Resolvins: a family of bioactive products of omega-3 fatty acids transformation circuits initiated by aspirin treatment that counter proinflammation signals", J Exp Med 196, 2002, pp. 1025-1037.
Spite, et al., "Resolvin D2 is a potent regulator of leukocytes and controls microbial sepsis", Nature 461, 2009, pp. 1287-1291.
Tjonahen, et al., "Resolvin E2: identification and anti-inflammatory actions: pivotal role of human 5-lipoxygenase in resolvin E series biosynthesis", Chem Biol 13(11), 2006, pp. 1193-1202.
van Gils, et al., "Molecular and Functional interactions among monocytes, platelets, and endothelial cells and their relevance for cardiovascular diseases", J Leukoc Biol 85(2), 2009, pp. 195-204.
Xu, et al., "Resolvins RvE1 and RvD1 attenuate inflammatory pain via central and peripheral actions", Nat Med 16, 2010, pp. 592-597.
Yanes, et al., "Metabolic oxidation regulates embryonic stem cell differentiation", Nat Chem Biol 6(6), 2010, pp. 411-417.
Yang, et al., "Decoding Functional Metabolomics with Docosahexaenoyl Ethanolamide (DHEA) Identifies Novel Bioactive Signals", The Journal of Biological Chemistry, vol. 286, No. 36, 2011, pp. 31532-31541.
Yang, et al., "Metabolomics-Lipidomics of Eicosanoids and Docosanoids Generated by Phagocytes", Curr Protoc Immunol. Nov. 2011; Chapter: Unit—14.26.
Bailes, et al, "Docosahexaenoic Acid Reduces Traumatic Axonal Injury in a Rodent Head Injury Model", Journal of Neurotrauma, vol. 27, No. 9, 2010, pp. 1617-1624.
De Petrocellis, et al., "Endocannabinoids and fatty acid amides in cancer, inflammation and related disorders" Chemistry and Physics of Lipids, No. 108, 2000, pp. 191-209.
Devane, et al., "Isolation and structure of a brain constituent that binds to the cannabinoid receptor", Science, vol. 258, 1992, pp. 1946-1949.
Di Marzo, et al., "Endocannabinoids: endogenous cannabinoid receptor ligands with neuromodulatory action", TINS, vol. 21, 1998, pp. 521-528.
Kozak, et al., "Oxidative metabolism of endocannabinoids", Prostaglandins Leukot. Essent. Fatty Acids, No. 66, 2002, pp. 211-220.
Pace-Asciak, et al., "The hepoxilins. A review", Adv. Exp. Med. Biol., No. 447, 1999, pp. 123-132.
Pavlopoulos, et al., "Cannabinoid receptors as therapeutic targets", Curr. Pharm. Des., No. 12, 2006, pp. 1751-1769.
Preissner, "Altered polymorphonuclear leukocyte responses in psoriasis: chemotaxis and degranulation", Br. J. Dermatol., No. 109, 1983, pp. 1-8.
Serhan, et al., "Resolving inflammation: dual anti-inflammatory and proresolution lipid mediators", Nat Rev Immunol., No. 8(5), 2008, pp. 349-361.
Sheskin, et al., "Structural requirements for binding of anandamide-type compounds to the brain cannabinoid receptor", J Med Chem, No. 40, 1997, pp. 659-667.
Ueda, et al., "Lipoxygenase-catalyzed oxygenation of arachidonylethanolamide, a cannabinoid receptor agonist", Biochimica et Biophysica Acta, No. 1254, 1995, pp. 127-134.
Weyrich, et al., "Platelets: signaling cells in the immunce continuum", Trends Immunol., vol. 25, No. 9, 2004, pp. 489-495.
Zygmunt, "Vanilloid receptors on sensory nerves mediate the vasodilator action of anandamide", Nature, No. 400, 1999, pp. 452-457.

* cited by examiner

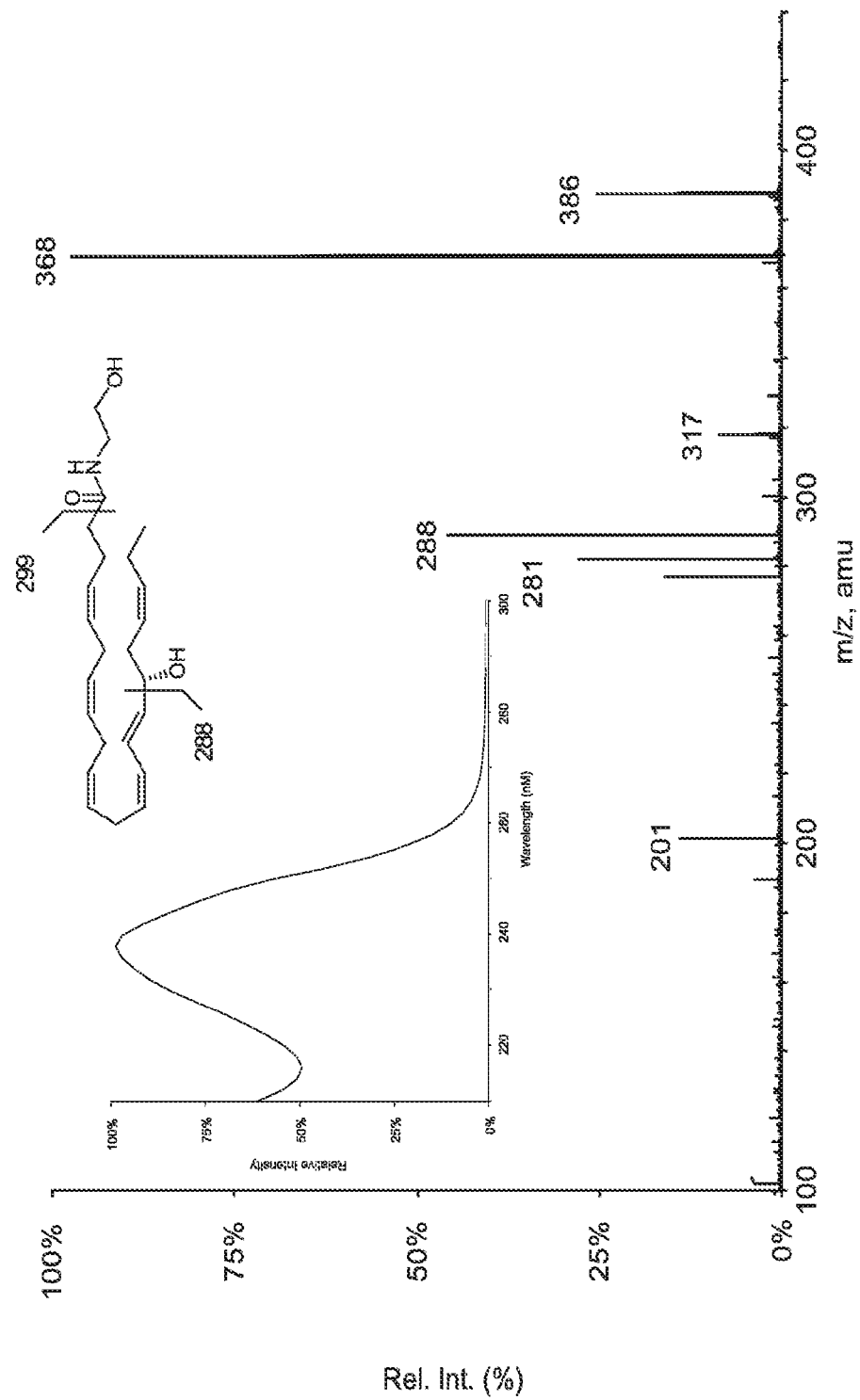
Supplemental Figure 1

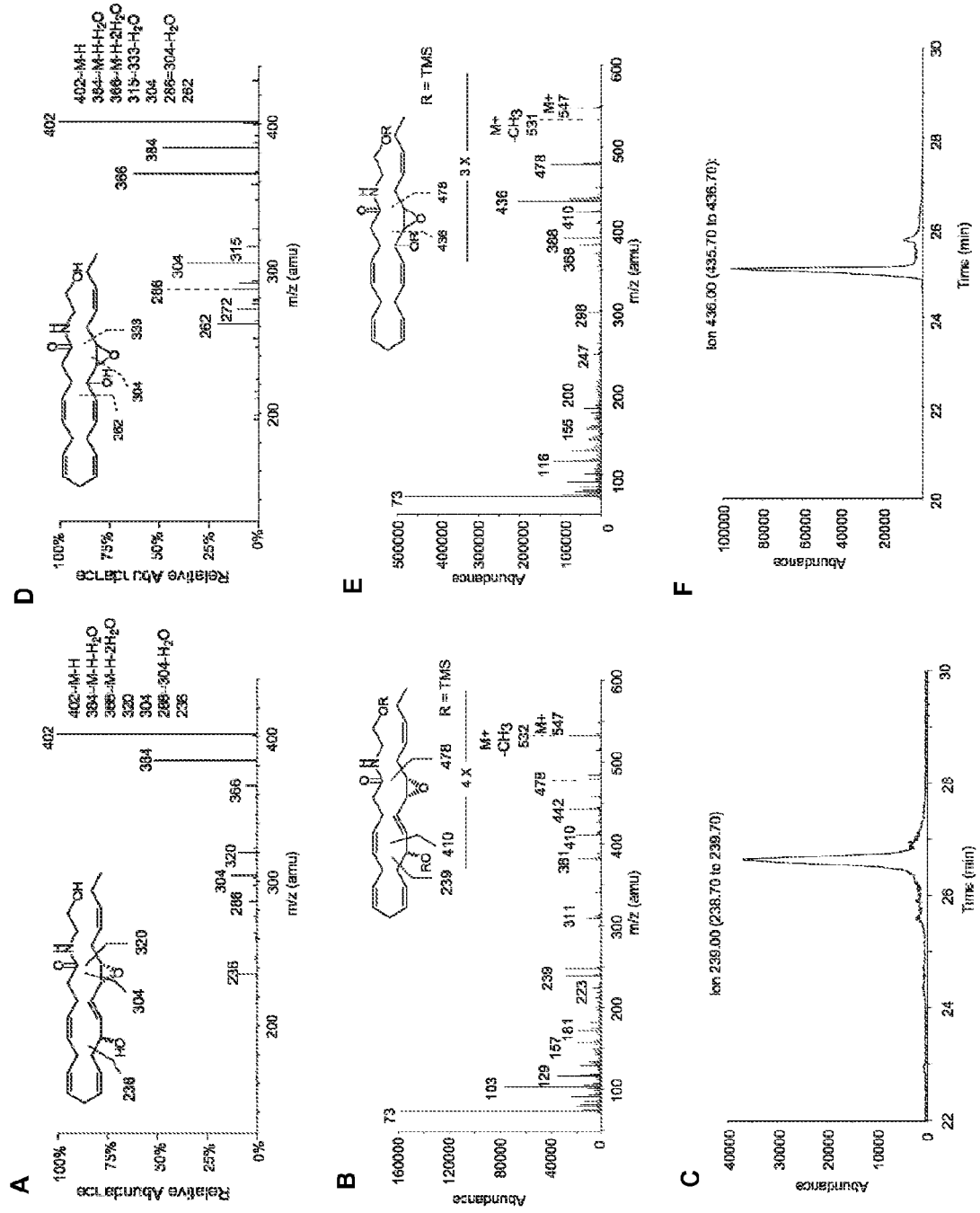
Supplemental Figure 2

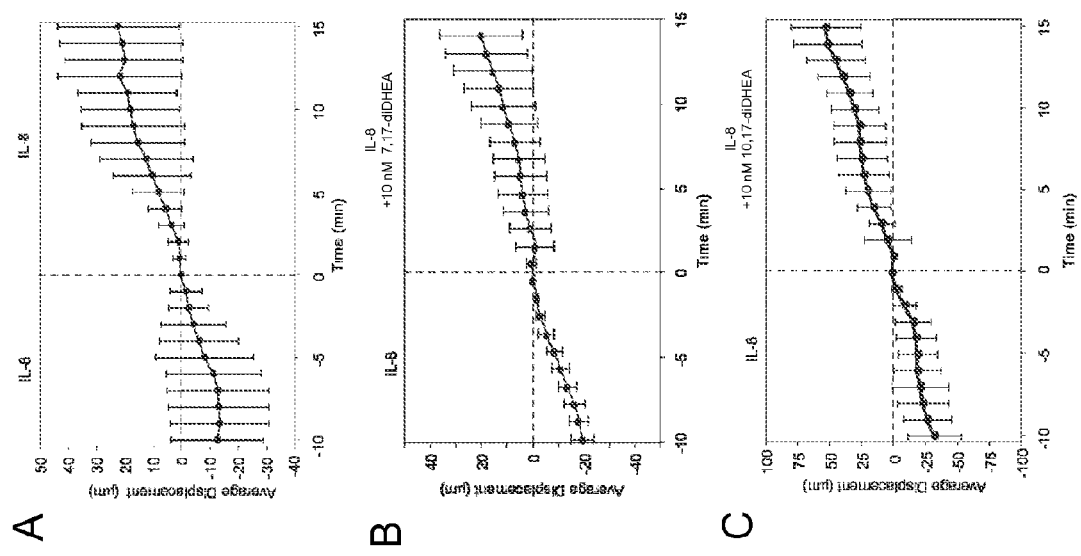
Supplemental Figure 3

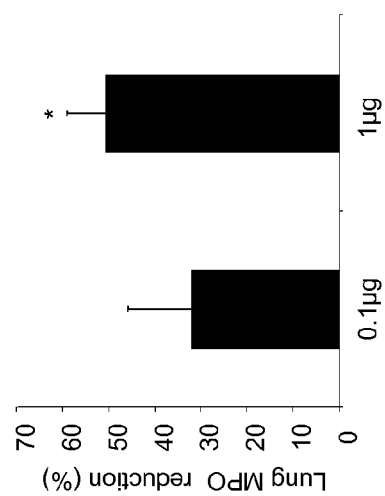
Supplemental Figure 4

DOCOSAHEXAENOYL ETHANOLAMIDES

CROSS REFERENCE TO RELATED APPLICATION(S)

This application is a National Stage application under 35 U.S.C. 371 of PCT/US2012/041510, filed on Jun. 8, 2012 and published as WO 2012/170791 A2 on Dec. 13, 2012, which claims benefit under 35 U.S.C. §119(e) to U.S. Provisional Application Ser. No. 61/495,705, entitled "DOCOSA-HEXAENOYL ETHANOLAMIDES", filed Jun. 10, 2011, the contents of which is incorporated herein by reference in its entirety.

STATEMENT REGARDING FEDERALLY SPONSORED RESEARCH

This invention was made with government support under Grant Numbers NS067686, AT005909, and DE019938, awarded by the National Institute of Health. The government has certain rights in the invention.

FIELD OF THE INVENTION

The invention relates generally to novel mono and dihydroxy analogues of docosahexaenoic acid (DHA) a having a hydroxyl group at C-17 of the carbon chain or an epoxide at C-16/C-17 and optionally, a second hydroxyl group at either the C-4, C-7 or C-10 positions of the carbon chain. The present invention also provides novel mono hydroxyl analogues of docosahexaenoic acid having a hydroxyl group at C-13 with an epoxide at C16/C17, a thiol derivative at C-16 with a hydroxyl at C-17 or a dihydroxy compound having hydroxyl groups at C-4 and C-20.

BACKGROUND OF THE INVENTION

Neuroinflammation and local pro-inflammatory mediators are associated with neurodegenerative diseases as well as traumatic brain injury (1). In both scenarios, treatment with docosahexaenoic acid (DHA) reduces inflammation and local tissue injury. For example, DHA reduces the damage from impact acceleration injury and reduces β-amyloid precursor, a marker of axonal injury in vivo relevant in traumatic brain injury (2). Also, DHA reduces ischemic stroke in rats via production of neuroprotectin D1, which acts on leukocytes and reduces leukocyte infiltration, leukocyte-mediator tissue damage and regulates NF-κB (3). Neuroprotectin D1 stimulates neuronal stem cell differentiation (4) and has potent anti-inflammatory and pro-resolving actions in several in vivo disease models (5-7). D series resolvins are biosynthesized from DHA in brain tissue and resolving inflammatory exudates (7,8). Resolvin D1 and resolvin D2 display potent stereoselective actions that are anti-inflammatory, pro-resolving and reduce pain signaling, and act in the pico- to nano-molar range in vivo, a dose range where DHA itself displays no demonstrable action (9-11). Hence, the metabolome and metabolic fate of DHA is of interest in the resolution of pain, inflammation and tissue injury.

Another metabolic fate of DHA in brain is conversion to docosahexaenoyl ethanolamide (DHEA), which is thought to be produced by the same pathway as N-acyl-arachidonoyl-ethanolamide (AEA, anandamide) (12). DHEA is directly related to dietary intake of DHA and is enriched in brain tissue at comparable levels to AEA (13). AEA is an endocannabinoid that regulates neurofunctions and the immune system via CB1 and CB2 receptors (14-17).

Therefore, a need exists for a further understanding of, an exploration or and identification of new useful materials previously not appreciated as potent biological mediators of interest.

BRIEF SUMMARY OF THE INVENTION

Neuroinflammation and traumatic brain injury involve activation of inflammatory cells and production of local pro-inflammatory mediators that can amplify tissues damage. Using an LC-UV-MS-MS based lipidomic in tandem with functional screening at the single cell level in microfluidic chambers, we identified a series of novel bioactive oxygenated docosahexaenoic ethanolamide-(DHEA) derived products that regulated leukocyte motility. These included 10,17-dihydroxydocosahexaenoyl ethanolamide (10,17-diHDHEA) and 15-hydroxy-16(17)-epoxy-docosapentaenoyl ethanolamide (15-HEDPEA), each of which was an agonist of recombinant CB2 receptors with $EC_{50}$ $3.9 \times 10^{10}$ M and $1.0 \times 10^{-10}$ M. In human whole blood, 10,17-diHDHEA and 15-HEDPEA at concentrations as low as 10 pM each prevented formation of platelet-leukocyte aggregates involving either platelet-monocyte or platelet-PMN. In vivo, 15-HEDPEA was organ protective in mouse reperfusion second organ injury. Together these results indicate that DHEA oxidative metabolism produces potent novel molecules with anti-inflammatory and organ protective properties.

The present invention surprisingly provides novel mono and dihydroxy analogues of docosahexaenoic acid (DHA) having a hydroxyl group at C-17 of the carbon chain or an epoxide at C-16/C-17 and optionally, a second hydroxyl group at either the C-4, C-7 or C-10 positions of the carbon chain. The present invention also provides novel mono hydroxyl analogues of docosahexaenoic acid having a hydroxyl group at C-13 with an epoxide at C16/C17, a thiol derivative at C-16 with a hydroxyl at C-17 or a dihydroxy compound having hydroxyl groups at C-4 and C-20. These materials are biogenically derived and isolated from media.

In one embodiment, the invention pertains to a new and useful DHA analogue such as a compound comprising the formula (I):

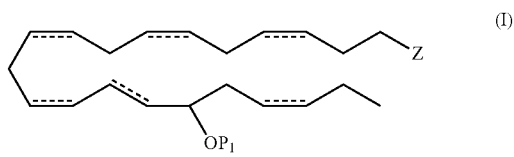

wherein $P_1$ is a protecting group or a hydrogen atom;
wherein ----- is a double bond;
wherein Z is —C(O)OR$^d$, —C(O)NR$^c$R$^c$, —C(O)NR$^c$R$^c$—OH, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different $R^a$ or suitable $R^b$ groups;

each $R^b$ is independently selected from =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR^d$, —$OC(O)NR^cR^c$, —$OC(NH)NR^cR^c$, —$OC(NR^a)NR^cR^c$, —$[NHC(O)]_nR^d$, —$[NR^aC(O)]_nR^d$, —$[NHC(O)]_nOR^d$, —$[NR^aC(O)]_nOR^d$, —$[NHC(O)]_nNR^cR^c$, —$[NR^aC(O)]_nNR^cR^c$, —$[NHC(NH)]_nNR^cR^c$ or —$[NR^aC(NR^a)]_nNR^cR^c$;

each n, independently is an integer from 0 to 3; and each $R^d$, independently is a protecting group or $R^a$;

or a pharmaceutically acceptable salt thereof. In one aspect, when Z is —$C(O)OR^d$, then $R^d$ for Z is not a hydrogen. In certain aspects, $P_1$ is a hydrogen atom. In another aspect, the double bonds at the C-4/5, 7/8, 10/11, 13/14 and 19/20 positions are each of Z configuration. In one aspect, the double bond at C-15/16 is of E configuration.

A particular isomer of interest of the DHA analogue (I) is (Ia) comprising the formula:

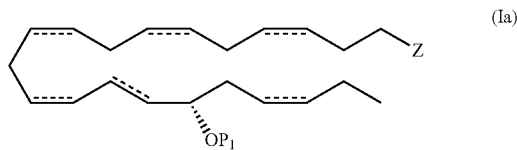

(Ia)

wherein $P_1$, ------, Z, $R^a$, $R^b$, $R^c$, $R^d$ and n are as previously defined. In one embodiment, $P_1$ is a hydrogen atom.

Another isomer of interest of the DHA analogue (I) is (Ib) comprising the formula:

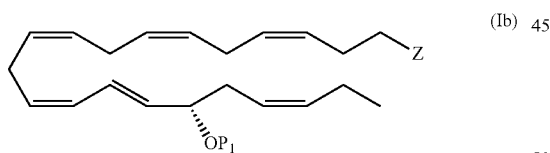

(Ib)

wherein $P_1$, Z, $R^a$, $R^b$, $R^c$, $R^d$ and n are as previously defined. In one embodiment, $P_1$ is a hydrogen atom.

It should be understood that compounds (I) through (Ib) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (I) through (Ib). Purified compounds include that when Z is —$C(O)OR^d$, then $R^d$ for Z is a hydrogen.

In another aspect, the invention pertains to a new and useful DHA analogue such as a compound comprising the formula (II):

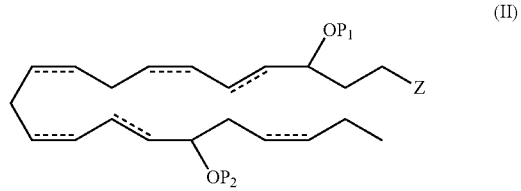

(II)

wherein $P_1$, ------, Z, $R^a$, $R^b$, $R^c$, $R^d$ and n are as previously defined. $P_2$, independently of $P_1$, is a protecting group or a hydrogen atom. In one aspect, when Z is —$C(O)OR^d$, then $R^d$ for Z is not a hydrogen. In one embodiment, $P_1$ and $P_2$ are both hydrogen atoms. In another embodiment, the double bonds at the C-7/8, 10/11, 13/14 and 19/20 positions are each of Z configuration.

In another aspect, the present invention provides new and useful DHA analogues such as:

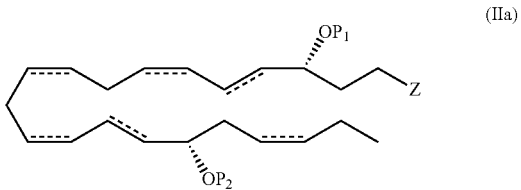

(IIa)

wherein $P_1$, $P_2$, ------, Z, $R^a$, $R^b$, $R^c$, $R^d$ and n are as previously defined. In one aspect, $P_1$ and $P_2$ are both hydrogen atoms. In still another aspect, the double bonds at C-7/8, 10/11, 13/14 and 19/20 positions are each of Z configuration.

In still another aspect, the present invention provides new and useful DHA analogues such as:

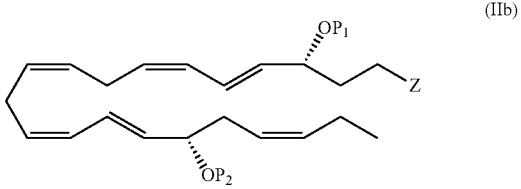

(IIb)

wherein $P_1$, $P_2$, Z, $R^a$, $R^b$, $R^c$, $R^d$ and n are as previously defined. In one embodiment, $P_1$ and $P_2$ are both hydrogen atoms.

It should be understood that compounds (II) through (IIb) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (II) through (IIb). Purified compounds include that when Z is —$C(O)OR^d$, then $R^d$ for Z is a hydrogen.

In another aspect, the present invention provides new and useful DHA analogues such as a compound comprising formula (III):

(III)

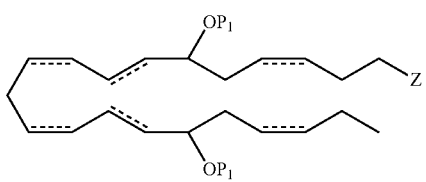

wherein $P_1$, $P_2$, ------, Z, $R^a$, $R^b$, $R^c$, $R^d$ and n are as previously defined, provided when Z is —C(O)OR$^d$, then $R^d$ for Z is not a hydrogen. In one embodiment, $P_1$ and $P_2$ are both hydrogen atoms. In another embodiment, the double bonds at the C-4/5, 10/11, 13/14 and 19/20 positions are each of Z configuration.

In still another aspect, the present invention provides new and useful DHA analogues such as a compound comprising the formula (IIIa):

(IIIa)

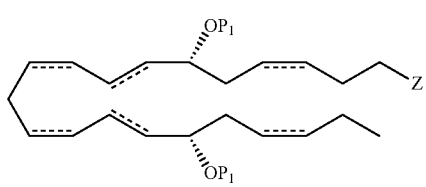

wherein $P_1$, $P_2$, ------, Z, $R^a$, $R^b$, $R^c$, $R^d$, $R_1$ and n are as previously defined. In one aspect, $P_1$ and $P_2$ are both hydrogen atoms. In another embodiment, the double bonds at the C-4/5, 10/11, 13/14 and 19/20 positions are each of Z configuration.

In still another aspect, the present invention provides new and useful DHA analogues such as a compound comprising the formula (IIIb):

(IIIb)

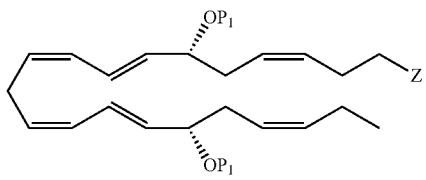

wherein $P_1$, $P_2$, Z, $R^a$, $R^b$, $R^c$, $R^d$, $R_2$ and n are as previously defined. In one aspect, $P_1$ and $P_2$ are both hydrogen atoms.

It should be understood that compounds (III) through (IIIb) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (III) through (IIIb). Purified compounds include that when Z is —C(O)OR$^d$, then $R^d$ for Z is a hydrogen.

In yet another aspect, the present invention provides new and useful DHA analogues such as a compound comprising formula (IV):

(IV)

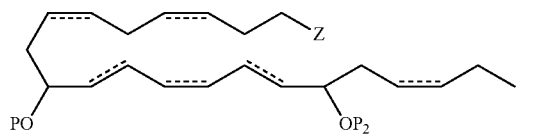

wherein $P_1$, $P_2$, ------, Z, $R^a$, $R^b$, $R^c$, $R^d$ and n are as previously defined, provided when Z is —C(O)OR$^d$, then $R^d$ for Z is not a hydrogen. In one embodiment, $P_1$ and $P_2$ are both hydrogen atoms. In one embodiment, the double bonds at C-4/5, 7/8, 13/14 and 19/20 positions are each of Z configuration.

In still another aspect, the present invention provides new and useful DHA analogues such as a compound comprising the formula (IVa):

(IVa)

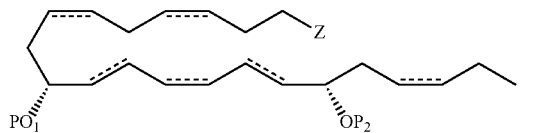

wherein $P_1$, $P_2$, ------, Z, $R^a$, $R^b$, $R^c$, $R^d$, $R_1$ and n are as previously defined. In one aspect, $P_1$ and $P_2$ are both hydrogen atoms. In another embodiment, the double bonds at C-4/5, 7/8, 13/14 and 19/20 positions are each of Z configuration.

In still another aspect, the present invention provides new and useful DHA analogues such as a compound comprising the formula (IVb):

(IVb)

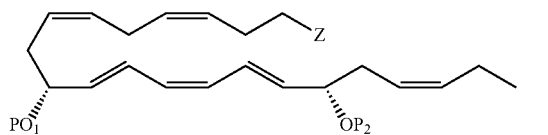

wherein $P_1$, $P_2$, Z, $R^a$, $R^b$, $R^c$, $R^d$, $R_1$ and n are as previously defined. In one aspect, $P_1$ and $P_2$ are both hydrogen atoms.

It should be understood that compounds (IV) through (IVb) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (IV) through (IVb). Purified compounds include that when Z is —C(O)OR$^d$, then $R^d$ for Z is a hydrogen.

In another aspect, the invention provides a compound comprising the formula (V):

(V)

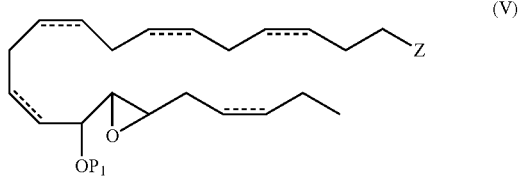

wherein $P_1$, ≈≈≈, Z, $R^a$, $R^b$, $R^c$, $R^d$ and n are as previously defined, provided when Z is —C(O)OR$^d$, then $R^d$ for Z is not a hydrogen. In one aspect, $P_1$ is a hydrogen atom. In another aspect, the double bonds at C-4/5, 7/8, 10/11 and 19/20 positions are each of Z configuration.

In still yet another aspect, the present invention provides a compound comprising the formula (Va):

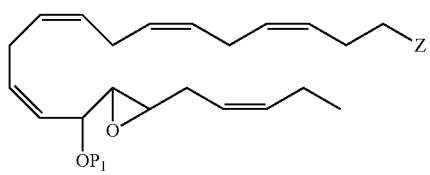

(Va)

wherein $P_1$, Z, $R^a$, $R^b$, $R^c$, $R^d$, $R_1$ and n are as previously defined. In one aspect, $P_1$, is a hydrogen atom. In another aspect, Z is —C(O)OR$^d$ and $R^d$ of Z is a hydrogen atom.

It should be understood that compounds (V) and (Va) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (V) and (Va). Purified compounds include that when Z is —C(O)OR$^d$, then $R^d$ for Z is a hydrogen.

In another aspect, the present invention provides new and useful DHA analogues such as a compound comprising the formula (VI):

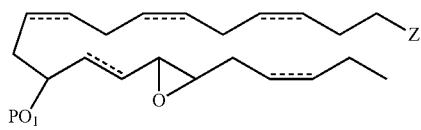

(VI)

wherein $P_1$, Z, $R^a$, $R^b$, $R^c$, $R^d$ and n are as previously defined.

In one aspect, $P_1$ is a hydrogen atom. In another aspect, Z is —C(O)OR$^d$ and $R^d$ of Z is a hydrogen atom. In another embodiment, the double bonds at the C-4/5, 7/8, 10/11 and 19/20 positions are each of Z configuration.

In another aspect, the present invention provides new and useful DHA analogues such as a compound comprising the formula (VIa):

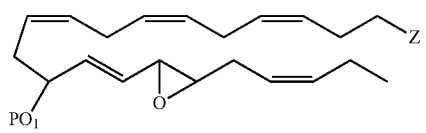

(VIa)

wherein $P_1$, Z, $R^a$, $R^b$, $R^c$, $R^d$, $R_1$ and n are as previously defined. In one aspect, $P_1$ is a hydrogen atom.

It should be understood that compounds (VI) and (VIa) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (VI) and (VIa). Purified compounds include that when Z is —C(O)OR$^d$, then $R^d$ for Z is a hydrogen.

In another aspect, the present invention provides new and useful DHA analogues such as a compound comprising the formula (VII):

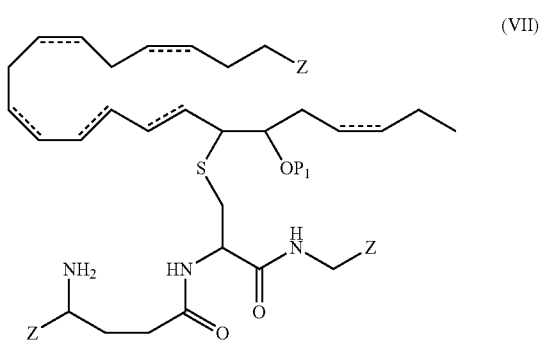

(VII)

wherein $P_1$, each Z independently, $R^a$, $R^b$, $R^c$, $R^d$ and n are as previously defined.

In one aspect, $P_1$ is a hydrogen atom. In another aspect, each Z is —C(O)OR$^d$ and $R^d$ of Z is a hydrogen atom. In another embodiment, the double bonds at the C-4/5, 7/8 and 19/20 positions are each of Z configuration.

In another aspect, the present invention provides new and useful DHA analogues such as a compound comprising the formula (VIIa):

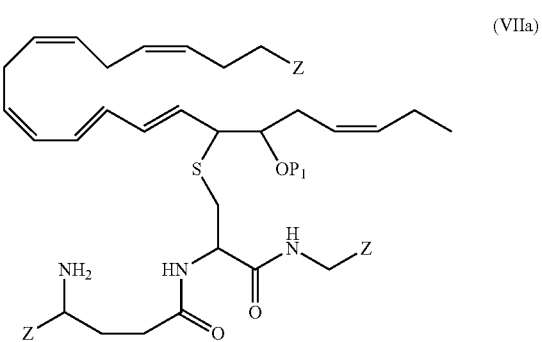

(VIIa)

wherein $P_1$, each Z independently, $R^a$, $R^b$, $R^c$, $R^d$, $R_1$ and n are as previously defined. In one aspect, $P_1$ is a hydrogen atom.

It should be understood that compounds (VII) and (VIIa) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (VII) and (VIIa). Purified compounds include that when Z is —C(O)OR$^d$, then $R^d$ for Z is a hydrogen.

In yet another aspect, the present invention provides new and useful DHA analogues such as a compound comprising formula (VIII):

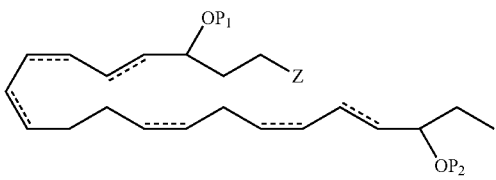

(VIII)

wherein $P_1$, $P_2$, -----, Z, $R^a$, $R^b$, $R^c$, $R^d$ and n are as previously defined, provided when Z is —C(O)OR$^d$, then R$^d$ for Z is not a hydrogen. In one embodiment, $P_1$ and $P_2$ are both hydrogen atoms. In one embodiment, the double bonds at C-7/8, 13/14 and 16/17 positions are each of Z configuration.

In still another aspect, the present invention provides new and useful DHA analogues such as a compound comprising the formula (VIIIa):

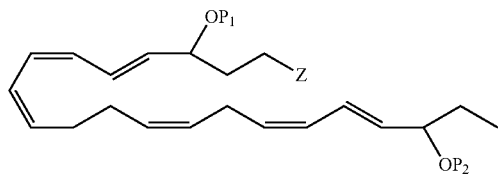

(VIIIa)

wherein $P_1$, $P_2$, -----, Z, $R^a$, $R^b$, $R^c$, $R^d$, $R_1$ and n are as previously defined. In one aspect, $P_1$ and $P_2$ are both hydrogen atoms.

It should be understood that compounds (VIII) and (VIIIa) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (VIII) and (VIIIa). Purified compounds include that when Z is —C(O)OR$^d$, then R$^d$ for Z is a hydrogen.

In another embodiment, the hydrogen atom of the hydroxyl bearing carbon atom(s), e.g, at —OP$_1$ and/or OP$_2$ can be replaced with an alkyl group, such as a methyl group, to help prevent oxidation for any of compounds I through VIIIa.

In another aspect, the present invention provides pharmaceutical compositions comprising one or more compounds of the invention, with or without other active pharmaceutical ingredients, in admixture with a pharmaceutically acceptable vehicle. Such a preparation can be administered according to the methods of the current invention.

In yet another aspect, the present invention is drawn to methods for treating or preventing inflammation or inflammatory disease in a mammal. The method involves administering a prophylactically or therapeutically effective amount of at least one compound of the invention, or a pharmaceutical composition thereof. For example, the compounds of the invention can be used to treat or prevent inflammation, cancer, neurodegeneration, memory loss, wrinkles, psoriasis, dandruff or dermatitis by administering to an individual in need thereof, an effective amount of any of the compounds described herein.

Additionally, the compounds of the invention can be used to neural development, fetal development, homeostasis, tissue remodeling, or wound repair by administering to an individual in need thereof, an effective amount of any of the compounds described herein.

Additional features and advantages of the invention will become more apparent from the following detailed description and claims While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

Figure 1:
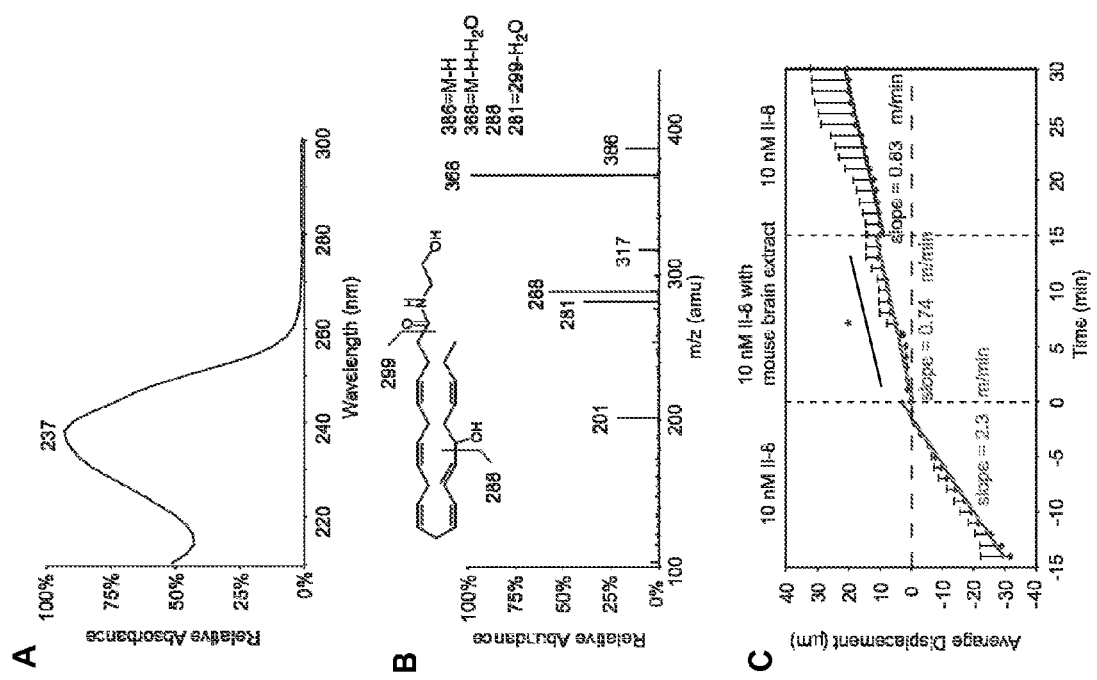
FIG. 1. Identification of hydroxydocosahexaenoylethanolamide and functional screening of DHEA brain metabolome. a) Online UV, b) tandem mass spectrum of 17-HDHEA. Inset shows fragment assignments for HDHEA mass spectrum, and c) representative average of PMN directional migration velocity in 0-10 nM IL-8 gradient (µm/min) before and after metabolite mixtures were infused to the chamber. The mixtures were isolated from mouse brain homogenate incubated with 5 µg DHEA. Error bars represent migration distance±S.D. for mean of 26 single PMN (n=3 separate donors). *P<0.01 for IL-8 versus brain extracts.

Supplemental FIG. 1. Representative tandem mass and UV spectrum of 17-HDHEA prepared from incubations of DHEA with 15-lipoxygenase (see Methods for details).

Figure 2:
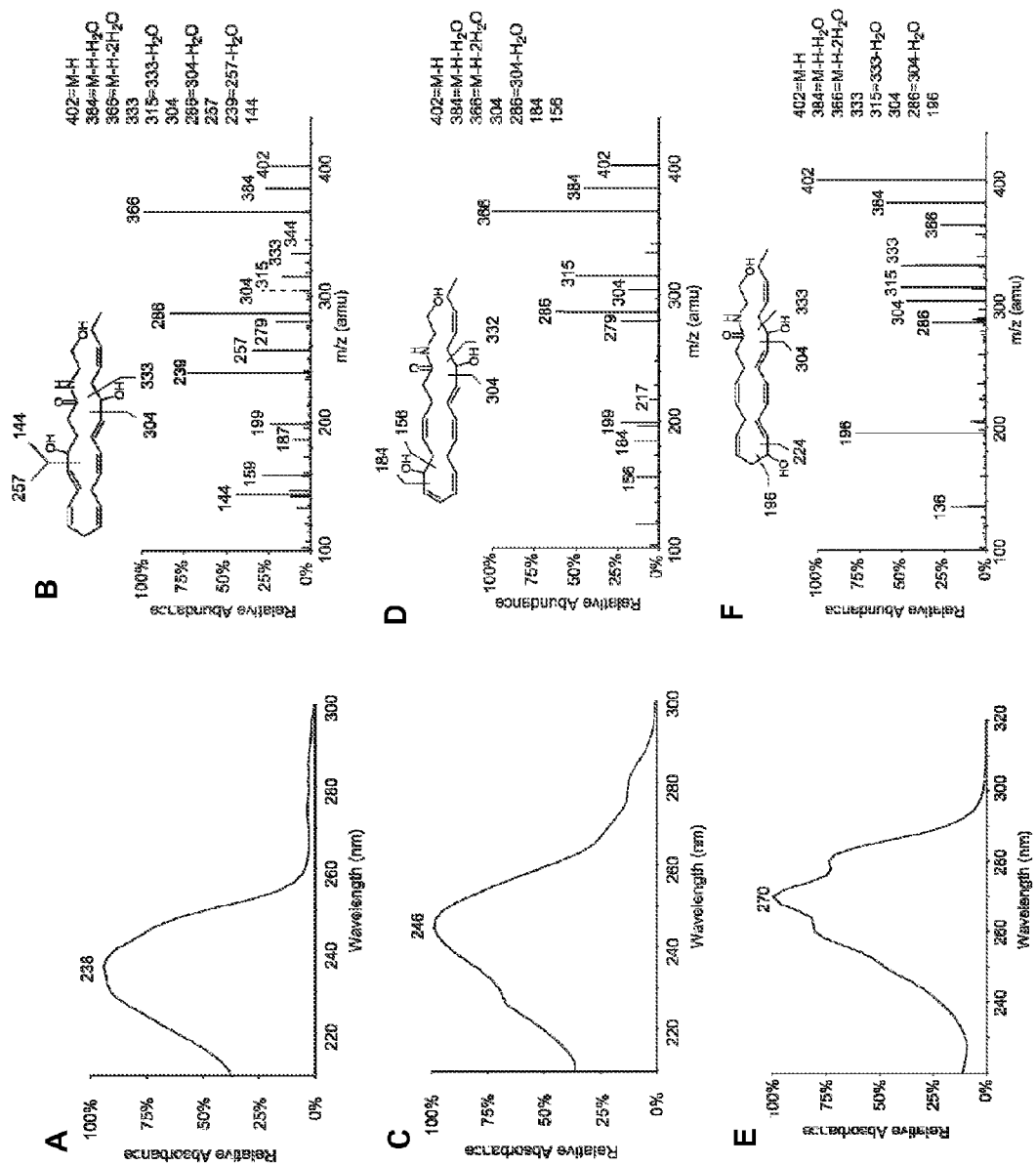
FIG. 2. DHEA metabolome via LC-UV-MS-MS based lipidomics. a-f) Online UV, fragment assignments shown in inset, and tandem mass spectrum of 4,17-diHDHEA, 7,17-diHDHEA and 10,17-diHDHEA.

Supplemental FIG. 2. DHEA metabolome via LC-UV-MS-MS-based lipidomics. (a-f) tandem mass spectrum and fragmentation assignments, GC-MS mass spectrum and dominant ion fragmentation assignments, and selected ion chromatograph of 13-HEDPEA and 15-HEDPEA.

Figure 3:
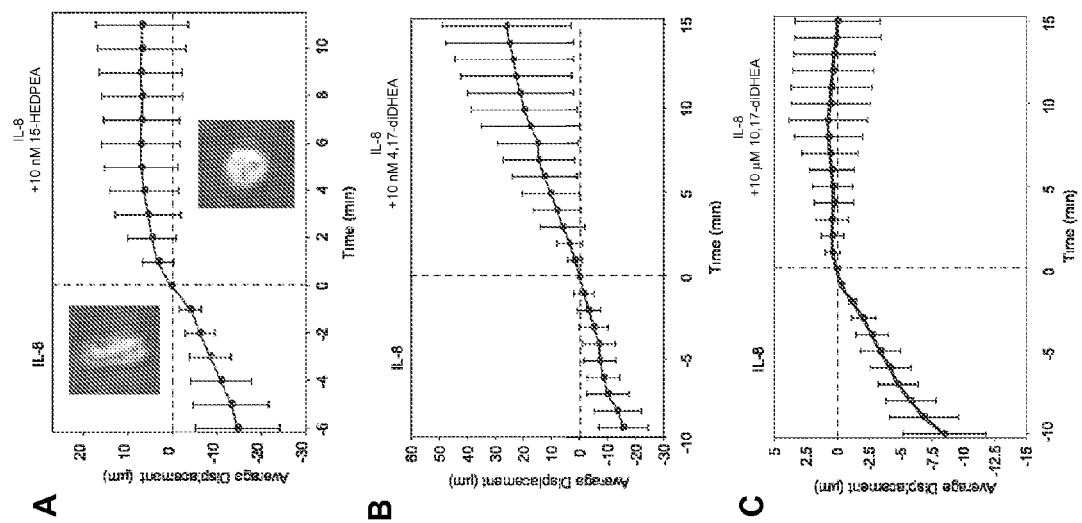
FIG. 3. Microfluidic chamber based screening of human PMN chemotaxis with DHEA derived products. a-c) Representative average PMN directional migration displacement against 0-10 nM IL-8 gradient from original positions (µm) before and after HPLC isolated DHEA derived products were individually infused to the chambers. Insets in a) show morphology of PMN before (left side) and after (right side) exposure to 10 nM 15-HEDPEA (average of 23-30 PMN in each panel).

Supplemental FIG. 3. Microfluidic chamber screening of human PMN chemotaxis. (a-c) Representative average PMN directional migration displacement against a 0-10 nM IL-8 gradient. Analyses were caned out as in FIGS. 1 and 3.

Figure 4:
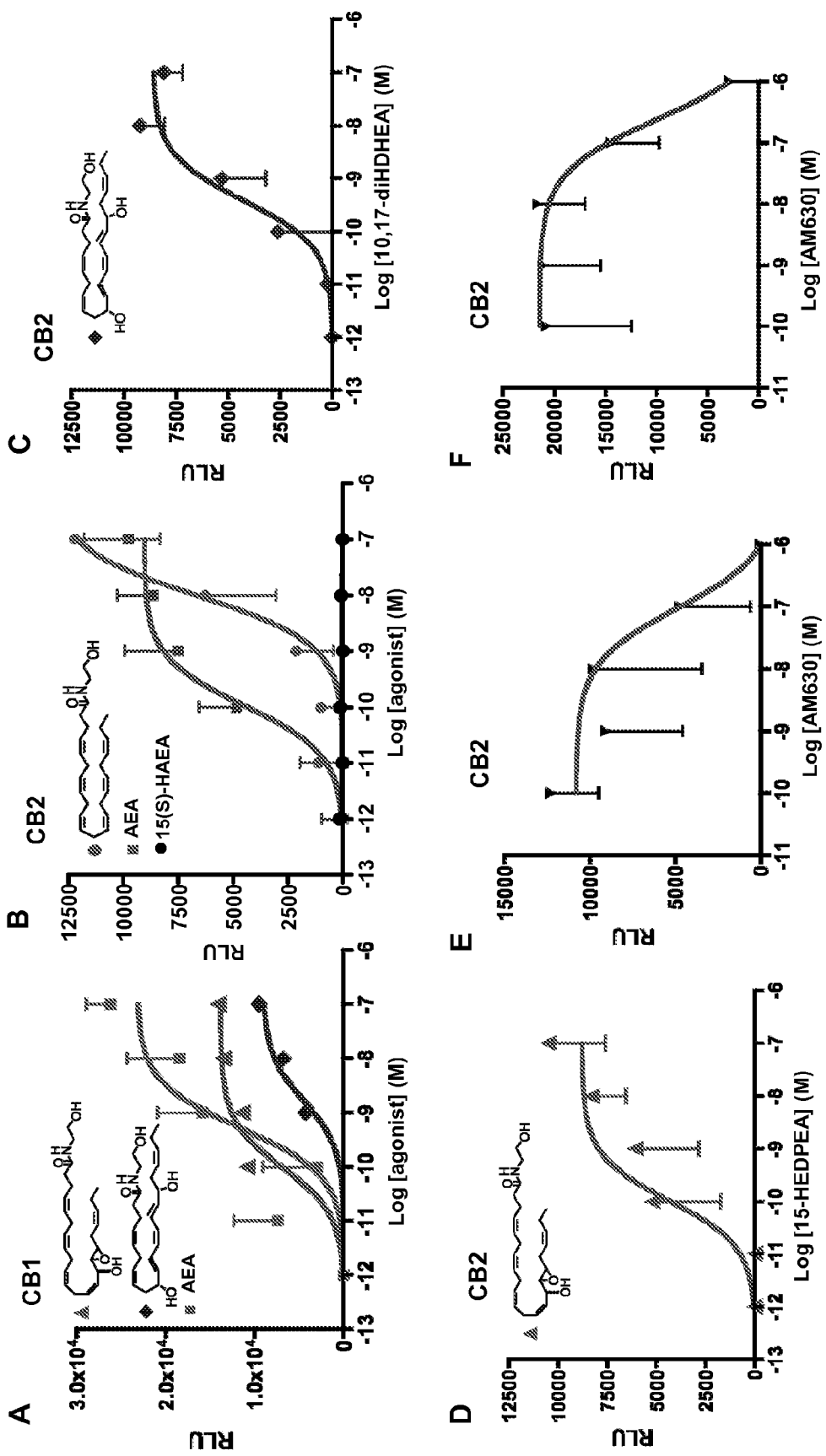
FIG. 4. GPCR CB1 and CB2 are activated by DHEA-derived products. HEK cells overexpressing CB1 or CB2 in a beta-arrestin system were incubated with indicated concentrations of compounds for 1 h in serum free DMEM at 37° C. Ligand receptor interactions were determined by increases in chemiluminescence generated upon interaction of the EA labeled beta arrestin with the Pro-Link tagged receptor (see Methods). Dose response activation of (a) GPCR CB1 and (b-d) GPCR CB2 with indicated compounds. CB2 receptor-ligand interactions were confirmed with dose response of CB2 specific inhibitor AM630 coincubated with GPCR CB2 over-expressed cell activation stimulated with (e) 15-HEDPEA (10 nM), and (f) AEA (10 nM) as positive control. AM630 inhibited GPCR CB2 interaction with 10,17S-diHDHEA at higher concentration (data not shown). See text for more details.

Supplemental FIG. 4. 15-HEDPEA is protective in mouse ischemia reperfusion second organ lung injury. Mice were subjected to hind limb ischemia for 1 hr using tourniquets. 15-HEDPEA was intravenously administered 5 min before tourniquet removal. After 2 hr reperfusion, mouse lungs were harvested and the tissue levels of myeloperoxidase (MPO) were determined using a mouse MPO ELISA. Results are expressed as reduction in lung associated decrease in leukocyte myeloperoxidase values (n=3-6).

DETAILED DESCRIPTION

Since AEA undergoes oxidative metabolism to bioactive molecules (16,18), the present invention addressed whether the beneficial actions of DHA treatment, for example, brain injury (2) can be regulated in part by conversion of DHEA to bioactive products.

The present invention provides the DHEA metabolome with identification of novel potent bioactive molecules that are organ protective in vivo. These novel bioactive products from DHEA were identified using LC-MS-MS-based lipidomics in tandem with functional single-cell screening in newly engineered microfluidic chambers and in vivo systems. These new bioactive products from DHEA may underlie some of the beneficial effects of DHA administration.

Abbreviations used throughout the specification:
AEA, anandamide, arachidonoylethanolamide;
DHEA, docosahexaenoylethanolamide;
4,17-diHDHEA, 4,17-dihydroxydocosa-5,7Z,10Z,13Z,15,19Z-hexaenoylethanolamide;
7,17-diHDHEA, 7,17-dihydroxydocosa-4Z,8E,10Z,13Z,15,19Z-hexaenoylethanolamide;
10,17-diHDHEA, 10,17-dihydroxydocosa-4Z,7Z,11,13Z,15,19Z-hexaenoylethanolamide;
17-HDHEA, 17-hydroxydocosa-4Z,7Z,10Z,13Z,15,19Z-hexaenoylethanolamide;
13-HEDPEA, 13-hydroxy-16(17)-epoxydocosa-4Z,7Z,10Z,14,19Z-pentaenoylethanolatnide;
15-HEDPEA, 15-hydroxy-16(17)-epoxydocosa-4Z,7Z,10Z,13Z,19Z-pentaenoylethanolamide;
LOX, lipoxygenase, abstracts hydrogen and inserts molecular oxygen in a stereoselective reaction with 1,4-cis-pentadiene units present in polyunsaturated fatty acids.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

"Compounds of the invention" refers to the mon-hydroxy, di-hydroxy, and/or epoxide DHA analogues and compounds encompassed by generic formulae disclosed herein and includes any specific compounds within those formulae whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention also include isotopically labeled compounds where one or more atoms have an atomic mass different from the atomic mass conventionally found in nature.

The compounds depicted throughout the specification contain ethylenically unsaturated sites. Where carbon carbon double bonds exist, the configurational chemistry can be either cis (Z) or trans (E) and the depictions throughout the specification are not meant to be limiting. The depictions are, in general, presented based upon the configurational chemistry of related DHA compounds, and although not to be limited by theory, are believed to possess similar configuration chemistry. The use of ≂ reflects this throughout the specification and claims so that both cis and trans isomers are contemplated. In certain embodiments the configuration of the ethylenic bond is known and is particularly described.

In one aspect of the invention, the compound(s) of the invention are substantially purified and/or isolated by techniques known in the art. The purity of the purified compounds is generally at least about 90%, preferably at least about 95%, and most preferably at least about 99% by weight.

Thus, the term "purified" as used herein does not require absolute purity; rather, it is intended as a relative term. For example, a purified DHA analogue can be one in which the subject DHA analogue is at a higher concentration than the analogue would be in its natural environment within an organism. For example, a DHA analogue of the invention can be considered purified if the analogue content in the preparation represents at least 50%, 60%, 70%, 80%, 85%, 90%, 92%, 95%, 98%, or 99% of the total analogue content of the preparation.

"Biological activity" and its contextual equivalents "activity" and "bioactivity" means that a compound elicits a statistically valid effect in any one biological test assays. Preferably, the threshold for defining an "active" compound will be reproducible and statistically valid effects of at least 25% deviation from untreated control at concentrations at or lower than 1 µM.

"Biological test assay" means a specific experimental procedure. Non-limiting examples of biological test assays include: 1) ligand binding, either direct or indirect, to a purified target, subcellular fraction, intact cell, or cell or tissue extract; 2) metabolic protection with enhanced half-life when exposed to a purified target, subcellular fraction, intact cell, cell or tissue extract, or administered to intact organism by any route; 3) prevention, reversal, or amelioration of cell- and tissue-based functional responses recognized by skilled artisans to represent surrogates for anti-inflammatory action (e.g., altered cytokine production and release); and 4) prevention, reversal, or amelioration of symptoms and/or disease processes in animal models of inflammation and inflammatory disease.

"Detectable label" means any chemical or biological modality which can be used to track, trace, localize, quantify, immobilize, purify, or identify compounds through appropriate means of detection known in the art. Non-limiting examples of detectable labels include fluorescence, phosphorescence, luminescence, radioactive or biospecific affinity capture labels.

"Electronegative group" is a chemical group that tends to acquire rather than lose electrons in its chemical interactions. Examples of electronegative groups include, but are not limited to, —$NO_2$, ammonium salts, sulfonyl groups, carbonyl groups, halogens, esters, carboxylic acids, nitriles, etc.

"In Situ" refers to and includes the terms "in vivo," "ex vivo" and "in vitro" as these terms are commonly recognized and understood by the skilled artisan. Moreover, the phrase "in situ" is employed herein in its broadest connotative and denotative context to identify an entity, cell, or tissue as found or in place, without regard to its source or origin, its condition or status or its duration or longevity at that location or position.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) salts formed when an basic proton is present in the parent compound such as acid addition salts, formed with inorganic acids such as hydrochloric acid, hydrobromic acid, sulfuric acid, nitric acid, phosphoric acid, and the like; or those formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton is present in the parent compound and either is replaced by a metal ion, e.g., an alkali metal ion, an alkaline earth ion, or an aluminum ion; or coordinates with an organic base such as ethanolamine, diethanolamine, triethanolamine, N-methylglucamine, triethylamine, propylamino, diazabicycloundecane and the like.

"Pharmaceutically acceptable vehicle" refers to a diluent, adjuvant, excipient or carrier with which a compound of the invention is administered.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

"Prodrug" refers to a derivative of a drug molecule that requires a transformation within the body to release the active drug. Prodrugs are frequently (though not necessarily) pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, imine, phosphonyl, phosphoryl or sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which contain different functional groups other than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2.sup.nd ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated (e.g., methyl and ethyl esters, acetate or propionate groups or glycol esters) or alkylated such as benzyl, and trityl ethers as well as alkyl ethers, tetrahydropyranyl ethers, trialkylsilyl ethers (e.g., TMS or TIPPS groups) and allyl ethers.

"Subject" means living organisms susceptible to conditions or diseases caused or contributed to by inflammation, inflammatory responses, vasoconstriction and myeloid suppression. Examples of subjects include humans, dogs, cats, cows, goats and mice. The term subject is further intended to include transgenic species such as, for example, transgenic mice.

"Alkyl" by itself or as part of another substituent refers to a saturated or unsaturated branched, straight-chain or cyclic monovalent hydrocarbon radical having the stated number of carbon atoms (i.e., C1-C6 means one to six carbon atoms) that is derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkanyl," "alkenyl" and/or "alkynyl" is used, as defined below. In preferred embodiments, the alkyl groups are (C1-C6) alkyl.

"Alkanyl" by itself or as part of another substituent refers to a saturated branched, straight-chain or cyclic alkyl derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In preferred embodiments, the alkanyl groups are (C1-C6) alkanyl.

"Alkenyl" by itself or as part of another substituent refers to an unsaturated branched, straight-chain or cyclic alkyl having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2 methyl prop 1-en 1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In preferred embodiments, the alkenyl group is (C2-C6) alkenyl.

"Alkynyl" by itself or as part of another substituent refers to an unsaturated branched, straight-chain or cyclic alkyl having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In preferred embodiments, the alkynyl group is (C2-C6) alkynyl.

"Alkyldiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to, methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Where it is specifically intended that the two valencies are on the same carbon atom, the nomenclature "alkylidene" is used. In preferred embodiments, the alkyldiyl group is (C1-C6) alkyldiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenos, defined infra).

"Alkdiyl" by itself or as part of another substituent refers to a saturated or unsaturated, branched, straight-chain or cyclic divalent hydrocarbon group having the stated number of carbon atoms (i.e., C1-C6 means from one to six carbon atoms) derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkdiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl-, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkandiyl, alkendiyl and/or alkandiyl is used. In a preferred embodiment, the alkdiyl group is (C1-C6) alkdiyl. Also preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkylenes, defined infra)

"Alkyleno" by itself or as part of another substituent refers to a straight-chain saturated or unsaturated alkyldiyl group having two terminal monovalent radical centers derived by the removal of one hydrogen atom from each of the two terminal carbon atoms of straight-chain parent alkane, alkene or alkyne. The locant of a double bond or triple bond, if present, in a particular alkyleno is indicated in square brackets. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, buta[1,3]diyno, etc.; and the like. Where specific levels of saturation are intended, the nomenclature alkano, alkeno and/or alkyno is used. In preferred embodiments, the alkyleno group is (C1-C6) or (C1-C3) alkyleno. Also preferred are straight-chain saturated alkano groups, e.g., methano, ethano, propano, butano, and the like.

"Heteroalkyl," Heteroalkanyl," "Heteroalkenyl," "Heteroalkynyl," "Heteroalkyldiyl" and "Heteroalkyleno" by themselves or as part of another substituent refer to alkyl, alkanyl, alkenyl, alkynyl, alkyldiyl and alkyleno groups, respectively, in which one or more of the carbon atoms are each independently replaced with the same or different heteratoms or heteroatomic groups. Typical heteroatoms and/or heteroatomic groups which can replace the carbon atoms include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or (C1-C6) alkyl.

"Cycloalkyl" and "Heterocycloalkyl" by themselves or as part of another substituent refer to cyclic versions of "alkyl" and "heteroalkyl" groups, respectively. For heteroalkyl groups, a heteroatom can occupy the position that is attached to the remainder of the molecule. Typical cycloalkyl groups include, but are not limited to, cyclopropyl; cyclobutyls such as cyclobutanyl and cyclobutenyl; cyclopentyls such as cyclopentanyl and cyclopentenyl; cyclohexyls such as cyclohexanyl and cyclohexenyl; and the like. Typical heterocycloalkyl groups include, but are not limited to, tetrahydrofuranyl (e.g., tetrahydrofuran-2-yl, tetrahydrofuran-3-yl, etc.), piperidinyl (e.g., piperidin-1-yl, piperidin-2-yl, etc.), morpholinyl (e.g., morpholin-3-yl, morpholin-4-yl, etc.), piperazinyl (e.g., piperazin-1-yl, piperazin-2-yl, etc.), and the like.

"Acyclic Heteroatomic Bridge" refers to a divalent bridge in which the backbone atoms are exclusively heteroatoms and/or heteroatomic groups. Typical acyclic heteroatomic bridges include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or (C1-C6) alkyl.

"Parent Aromatic Ring System" refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, tetrahydronaphthalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, tetrahydronaphthalene, triphenylene, trinaphthalene, and the like, as well as the various hydro isomers thereof.

"Aryl" by itself or as part of another substituent refers to a monovalent aromatic hydrocarbon group having the stated number of carbon atoms (i.e., C5-C15 means from 5 to 15 carbon atoms) derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like, as well as the various hydro isomers thereof. In preferred embodiments, the aryl group is (C5-C15) aryl, with (C5-C10) being even more preferred. Particularly preferred aryls are cyclopentadienyl, phenyl and naphthyl.

"Arylaryl" by itself or as part of another substituent refers to a monovalent hydrocarbon group derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. Where the number of carbon atoms in an arylaryl group are specified, the numbers refer to the carbon atoms comprising each parent aromatic ring. For example, (C5-C15) arylaryl is an arylaryl group in which each aromatic ring comprises from 5 to 15 carbons, e.g., biphenyl, triphenyl, binaphthyl, phenylnaphthyl, etc. Preferably, each parent aromatic ring system of an arylaryl group is independently a (C5-C15) aromatic, more preferably a (C5-C10) aromatic. Also preferred are arylaryl groups in which all of the parent aromatic ring systems are identical, e.g., biphenyl, triphenyl, binaphthyl, trinaphthylz, etc.

"Biaryl" by itself or as part of another substituent refers to an arylaryl group having two identical parent aromatic systems joined directly together by a single bond. Typical biaryl groups include, but are not limited to, biphenyl, binaphthyl, bianthracyl, and the like. Preferably, the aromatic ring systems are (C5-C15) aromatic rings, more preferably (C5-C10) aromatic rings. A particularly preferred biaryl group is biphenyl.

"Arylalkyl" by itself or as part of another substituent refers to an acyclic alkyl group in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophylethan-1-yl and the like. Where specific alkyl moieties are intended, the nomenclature arylalkanyl, arylakenyl and/or arylallcynyl is used. In preferred embodiments, the arylalkyl group is (C6-C21) arylalkyl, e.g., the alkanyl, alkenyl or alkynyl moiety of the arylalkyl group is (C1-C6) and the aryl moiety is (C5-C15). In particularly preferred embodiments the arylalkyl group is (C6-C13), e.g., the alkanyl, alkenyl or alkynyl moiety of the arylalkyl group is (C1-C3) and the aryl moiety is (C5-C10).

"Parent Heteroaromatic Ring System" refers to a parent aromatic ring system in which one or more carbon atoms are each independently replaced with the same or different heteroatoms or heteroatomic groups. Typical heteroatoms or heteroatomic groups to replace the carbon atoms include, but are not limited to, N, NH, P, O, S, S(O), S(O)$_2$, Si, etc. Specifically included within the definition of "parent heteroaromatic ring systems" are fused ring systems in which one or more of the rings are aromatic and one or more of the rings are saturated or unsaturated, such as, for example, benzodioxan, benzofuran, chromane, chromene, indole, indoline, xanthene, etc. Also included in the definition of "parent heteroaromatic ring system" are those recognized rings that include common substituents, such as, for example, benzopyrone and 1-methyl-1,2,3,4-tetrazole. Typical parent heteroaromatic ring systems include, but are not limited to, acridine, benzimidazole, benzisoxazole, benzodioxan, benzodioxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Heteroaryl" by itself or as part of another substituent refers to a monovalent heteroaromatic group having the stated number of ring atoms (e.g., "5-14 membered" means from 5 to 14 ring atoms) derived by the removal of one hydrogen atom from a single atom of a parent heteroaromatic ring system. Typical heteroaryl groups include, but are not limited to, groups derived from acridine, benzimidazole, benzisoxazole, benzodioxan, benzodiaxole, benzofuran, benzopyrone, benzothiadiazole, benzothiazole, benzotriazole, benzoxaxine, benzoxazole, benzoxazoline, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like, as well as the various hydro isomers thereof. In preferred embodiments, the heteroaryl group is a 5-14 membered heteroaryl, with 5-10 membered heteroaryl being particularly preferred.

"Heteroaryl-Heteroaryl" by itself or as part of another substituent refers to a monovalent heteroaromatic group derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. Where the number of atoms are specified, the numbers refer to the number of atoms comprising each parent heteroaromatic ring systems. For example, 5-15 membered heteroaryl-heteroaryl is a heteroaryl-heteroaryl group in which each parent heteroaromatic ring system comprises from 5 to 15 atoms, e.g., bipyridyl, tripuridyl, etc. Preferably, each parent heteroaromatic ring system is independently a 5-15 membered heteroaromatic, more preferably a 5-10 membered heteroaromatic. Also preferred are heteroaryl-heteroaryl groups in which all of the parent heteroaromatic ring systems are identical.

"Biheteroaryl" by itself or as part of another substituent refers to a heteroaryl-heteroaryl group having two identical parent heteroaromatic ring systems joined directly together by a single bond. Typical biheteroaryl groups include, but are not limited to, bipyridyl, bipurinyl, biquinolinyl, and the like. Preferably, the heteroaromatic ring systems are 5-15 membered heteroaromatic rings, more preferably 5-10 membered heteroaromatic rings.

"Heteroarylalkyl" by itself or as part of another substituent refers to an acyclic alkyl group in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylakenyl and/or heteroarylalkynyl is used. In preferred embodiments, the heteroarylalkyl group is a 6-21 membered heteroarylalkyl, e.g., the alkanyl, alkenyl or alkynyl moiety of the heteroarylalkyl is (C1-C6) alkyl and the heteroaryl moiety is a 5-15-membered heteroaryl. In particularly preferred embodiments, the heteroarylalkyl is a 6-13 membered heteroarylalkyl, e.g., the alkanyl, alkenyl or alkynyl moiety is (C1-C3) alkyl and the heteroaryl moiety is a 5-10 membered heteroaryl.

"Halogen" or "Halo" by themselves or as part of another substituent, unless otherwise stated, refer to fluoro, chloro, bromo and iodo.

"Haloalkyl" by itself or as part of another substituent refers to an alkyl group in which one or more of the hydrogen atoms is replaced with a halogen. Thus, the term "haloalkyl" is meant to include monohaloalkyls, dihaloalkyls, trihaloalkyls, etc. up to perhaloalkyls. For example, the expression "(C1-C2) haloalkyl" includes fluoromethyl, difluoromethyl, trifluoromethyl, 1-fluoroethyl, 1,1-difluoroethyl, 1,2-difluoroethyl, 1,1,1-trifluoroethyl, perfluoroethyl, etc.

The above-defined groups may include prefixes and/or suffixes that are commonly used in the art to create additional well-recognized substituent groups. As examples, "alkyloxy" or "alkoxy" refers to a group of the formula —OR", "alkylamine" refers to a group of the formula —NHR" and "dialkylamine" refers to a group of the formula —NR"R", where each R" is independently an alkyl. As another example, "haloalkoxy" or "haloalkyloxy" refers to a group of the formula —OR'", where R'" is a haloalkyl.

The present invention is also drawn to methods for treating arterial inflammation, arthritis, psoriasis, urticara, vasculitis, asthma, ocular inflammation, pulmonary inflammation, pulmonary fibrosis, seborrheic dermatitis, pustular dermatosis, or cardiovascular diseases in a subject by administration of one or more of the DHA analogs described herein. Disease states or conditions that are associated with inflammation such as the recruitment of neutrophils, leukocytes and/or cytokines are included within the general scope of inflammation and include, for example, Addiction, AIDS, Alcohol-related disorders, Allergy, Alzheimer's disease, Anesthesiology, Anti-infectives, Anti-inflammatory agents, Arthritis, Asthma, Atherosclerosis, Bone diseases, Breast cancer, Cancer, Cardiovascular diseases, Child health, Colon cancer, Congenital defects, Decision analysis, Degenerative neurologic disorders, Dementia, Dermatology, Diabetes mellitus, Diagnostics, Drug delivery, Drug discovery/screen, Endocrine disorders, ENT, Epidemiology, Eye diseases, Fetal and maternal medicine, Gastrointestinal disorders, Gene therapy, Genetic diagnostics, Genetics, Genitourinary disorders, Geriatric medicine, Growth and Development, Hearing, Hematologic disorders, Hepatobiliary disorders, Hypertension, Imaging, Immunology, Infectious diseases, Leukemia/lymphoma, Lung cancer, Metabolic disorders, Neonatology, Neurological disorders, Neuromuscular disorders, Nuclear medicine, Obesity/eating disorders, Orthopedic, Other, Parasitic diseases, Perinatal disorders, Pregnancy, Preventative medicine, Prostate cancer, Psychiatric disorders, Pulmonary disorders, Radiology, Renal disorders, Reproduction, Rheumatic diseases, Stroke, Surgical, Transplantation, Vaccines, Vascular medicine, Wound healing, oral infections, periodontal disease, brain injury, trauma and neuronal inflammation, and Women's health.

The pharmaceutical compositions of the invention include a "therapeutically effective amount" or a "prophylactically effective amount" of one or more of the DHA analogs of the invention. A "therapeutically effective amount" refers to an amount effective, at dosages and for periods of time necessary, to achieve the desired therapeutic result, e g, a diminishment or prevention of effects associated with various disease states or conditions. A therapeutically effective amount of the DHA analog may vary according to factors such as the disease state, age, sex, and weight of the individual, and the ability of the therapeutic compound to elicit a desired response in the individual. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the DHA analog and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a DHA analog of the invention is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one DHA analog, in combination with a pharmaceutically acceptable carrier.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1 19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention. Such solutions are useful for the treatment of conjunctivitis.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

The invention features an article of manufacture that contains packaging material and DHA analog formulation contained within the packaging material. This formulation contains an at least one DHA analog and the packaging material contains a label or package insert indicating that the formulation can be administered to the subject to treat one or more conditions as described herein, in an amount, at a frequency, and for a duration effective to treat or prevent such condition(s). Such conditions are mentioned throughout the specification and are incorporated herein by reference. Suitable DHA analogs are described herein.

The present invention surprisingly provides novel mono and dihydroxy analogues of docosahexaenoic acid (DHA) having a hydroxyl group at C-17 of the carbon chain or an epoxide at C-16/C-17 and optionally, a second hydroxyl group at either the C-4, C-7 or C-10 positions of the carbon chain. The present invention also provides novel mono hydroxyl analogues of docosahexaenoic acid having a hydroxyl group at C-13 with an epoxide at C16/C17, a thiol derivative at C-16 with a hydroxyl at C-17 or a dihydroxy compound having hydroxyl groups at C-4 and C-20. These materials are biogenically derived and isolated from media.

In one embodiment, the invention pertains to a new and useful DHA analogue such as a compound comprising the formula (I):

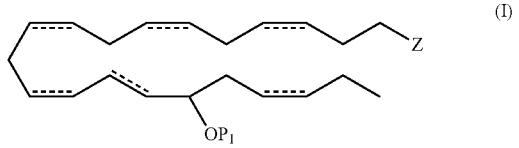

(I)

wherein $P_1$ is a protecting group or a hydrogen atom;
wherein ----- is a double bond;
wherein Z is —C(O)OR$^d$, —C(O)NR$^c$R$^c$, —C(O)NR$^c$R$^c$—OH, —C(O)H, —C(NH)NR$^c$R$^c$, —C(S)H, —C(S)OR$^d$, —C(S)NR$^c$R$^c$, or —CN;

each R$^a$, is independently selected from hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally include one or more of the same or different additional heteroatoms and which may optionally be substituted with one or more of the same or different R$^a$ or suitable R$^b$ groups;

each R$^b$ is independently selected from =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

each n, independently is an integer from 0 to 3; and
each R$^d$, independently is a protecting group or R$^a$;
or a pharmaceutically acceptable salt thereof. In one aspect, when Z is —C(O)OR$^d$, then R$^d$ for Z is not a hydrogen. In certain aspects, $P_1$ is a hydrogen atom. In another aspect, the double bonds at the C-4/5, 7/8, 10/11, 13/14 and 19/20 positions are each of Z configuration. In one aspect, the double bond at C-15/16 is of E configuration.

A particular isomer of interest of the DHA analogue (I) is (Ia) comprising the formula:

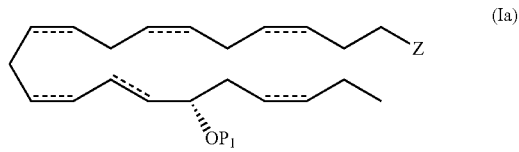

(Ia)

wherein $P_1$, -----, Z, R$^a$, R$^b$, R$^c$, R$^d$ and n are as previously defined. In certain aspects, $P_1$ is a hydrogen atom.

Another isomer of interest of the DHA analogue (I) is (Ib) comprising the formula:

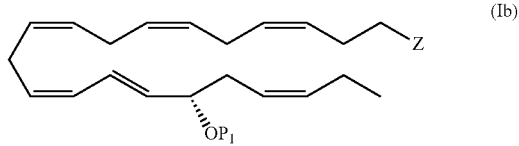

(Ib)

wherein $P_1$, Z, R$^a$, R$^b$, R$^c$, R$^d$ and n are as previously defined. In certain aspects, $P_1$ is a hydrogen atom.

It should be understood that compounds (I) through (Ib) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (I) through (Ib). Purified compounds include that when Z is —C(O)OR$^d$, then R$^d$ for Z is a hydrogen.

In another aspect, the invention pertains to a new and useful DHA analogue such as a compound comprising the formula (II):

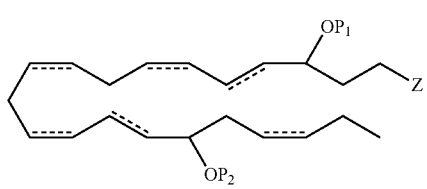

(II)

wherein P$_1$, $\texttt{-----}$, Z, R$^a$, R$^b$, R$^c$, R$^d$ and n are as previously defined. P$_2$, independently of P$_1$, is a protecting group or a hydrogen atom. In one aspect, when Z is —C(O)OR$^d$, then R$^d$ for Z is not a hydrogen. In one embodiment, P$_1$ and P$_2$ are both hydrogen atoms. In another embodiment, the double bonds at the C-7/8, 10/11, 13/14 and 19/20 positions are each of Z configuration.

In another aspect, the present invention provides new and useful DHA analogues such as:

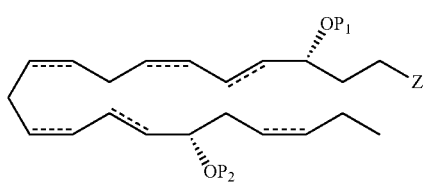

(IIa)

wherein P$_1$, P$_2$, $\texttt{-----}$, Z, R$^a$, R$^b$, R$^c$, R$^d$ and n are as previously defined. In one aspect, P$_1$ and P$_2$ are both hydrogen atoms. In still another aspect, the double bonds at C-7/8, 10/11, 13/14 and 19/20 positions are each of Z configuration.

In still another aspect, the present invention provides new and useful DHA analogues such as:

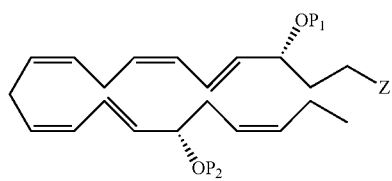

(IIb)

wherein P$_1$, P$_2$, Z, R$^a$, R$^b$, R$^c$, R$^d$ and n are as previously defined. In one embodiment, P$_1$ and P$_2$ are both hydrogen atoms.

It should be understood that compounds (II) through (IM) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (II) through (IIb). Purified compounds include that when Z is —C(O)OR$^d$, then R$^d$ for Z is a hydrogen.

In another aspect, the present invention provides new and useful DHA analogues such as a compound comprising formula (III):

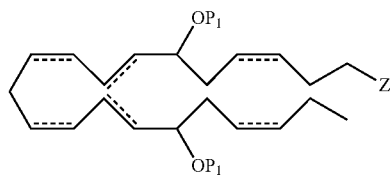

(III)

wherein P$_1$, P$_2$, $\texttt{-----}$, Z, R$^a$, R$^b$, R$^c$, R$^d$ and n are as previously defined, provided when Z is —C(O)OR$^d$, then R$^d$ for Z is not a hydrogen. In one embodiment, P$_1$ and P$_2$ are both hydrogen atoms. In another embodiment, the double bonds at the C-4/5, 10/11, 13/14 and 19/20 positions are each of Z configuration.

In still another aspect, the present invention provides new and useful DHA analogues such as a compound comprising the formula (IIIa):

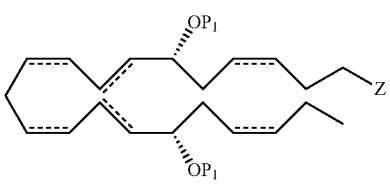

(IIIa)

wherein P$_1$, P$_2$, $\texttt{-----}$, Z, R$^a$, R$^b$, R$^c$, R$^d$, R$_1$ and n are as previously defined. In one aspect, P$_1$ and P$_2$ are both hydrogen atoms. In another embodiment, the double bonds at the C-4/5, 10/11, 13/14 and 19/20 positions are each of Z configuration.

In still another aspect, the present invention provides new and useful DHA analogues such as a compound comprising the formula (IIIb):

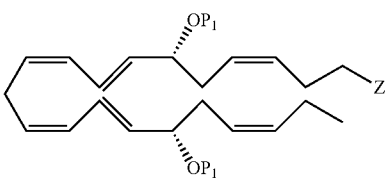

(IIIb)

wherein P$_1$, P$_2$, Z, R$^a$, R$^b$, R$^c$, R$^d$, R$_2$ and n are as previously defined. In one aspect, P$_1$ and P$_2$ are both hydrogen atoms.

It should be understood that compounds (III) through (IIIb) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (III) through (IIIb). Purified compounds include that when Z is —C(O)OR$^d$, then R$^d$ for Z is a hydrogen.

In yet another aspect, the present invention provides new and useful DHA analogues such as a compound comprising formula (IV):

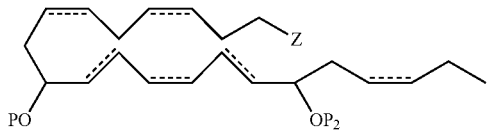

(IV)

wherein $P_1$, $P_2$, -----, Z, $R^a$, $R^b$, $R^c$, $R^d$ and n are as previously defined, provided when Z is —C(O)OR$^d$, then R$^d$ for Z is not a hydrogen. In one embodiment, $P_1$ and $P_2$ are both hydrogen atoms. In one embodiment, the double bonds at C-4/5, 7/8, 13/14 and 19/20 positions are each of Z configuration.

In still another aspect, the present invention provides new and useful DHA analogues such as a compound comprising the formula (IVa):

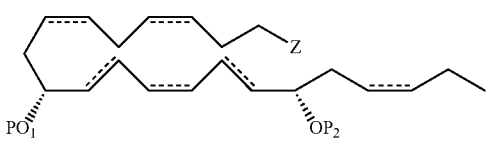

(IVa)

wherein $P_1$, $P_2$, -----, Z, $R^a$, $R^b$, $R^c$, $R^d$, $R_1$ and n are as previously defined. In one aspect, $P_1$ and $P_2$ are both hydrogen atoms. In another embodiment, the double bonds at C-4/5, 7/8, 13/14 and 19/20 positions are each of Z configuration.

In still another aspect, the present invention provides new and useful DHA analogues such as a compound comprising the formula (IVb):

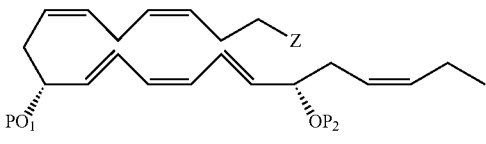

(IVb)

wherein $P_1$, $P_2$, Z, $R^a$, $R^b$, $R^c$, $R^d$, $R_1$ and n are as previously defined. In one aspect, $P_1$ and $P_2$ are both hydrogen atoms.

It should be understood that compounds (IV) through (IVb) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (IV) through (IVb). Purified compounds include that when Z is —C(O)OR$^d$, then R$^d$ for Z is a hydrogen.

In another aspect, the invention provides a compound comprising the formula (V):

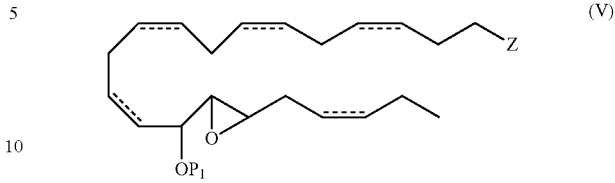

(V)

wherein $P_1$, -----, Z, $R^a$, $R^b$, $R^c$, $R^d$ and n are as previously defined, provided when Z is —C(O)OR$^d$, then R$^d$ for Z is not a hydrogen. In one aspect, $P_1$ is a hydrogen atom. In another aspect, the double bonds at C-4/5, 7/8, 10/11 and 19/20 positions are each of Z configuration.

In still yet another aspect, the present invention provides a compound comprising the formula (Va):

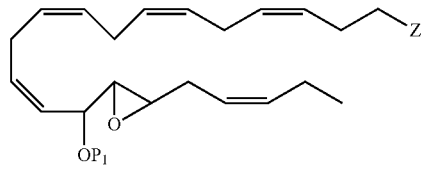

(Va)

wherein $P_1$, Z, $R^a$, $R^b$, $R^c$, $R^d$, $R_1$ and n are as previously defined. In one aspect, $P_1$, is a hydrogen atom. In another aspect, Z is —C(O)OR$^d$ and R$^d$ of Z is a hydrogen atom.

It should be understood that compounds (V) and (Va) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (V) and (Va). Purified compounds include that when Z is —C(O)OR$^d$, then R$^d$ for Z is a hydrogen.

In another aspect, the present invention provides new and useful DHA analogues such as a compound comprising the formula (VI):

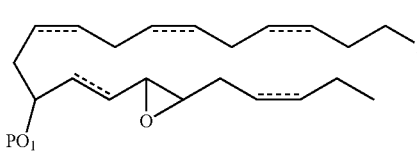

(VI)

wherein $P_1$, Z, $R^a$, $R^b$, $R^c$, $R^d$ and n are as previously defined.

In one aspect, $P_1$ is a hydrogen atom. In another aspect, Z is —C(O)OR$^d$ and R$^d$ of Z is a hydrogen atom. In another embodiment, the double bonds at the C-4/5, 7/8, 10/11 and 19/20 positions are each of Z configuration.

In another aspect, the present invention provides new and useful DHA analogues such as a compound comprising the formula (VIa):

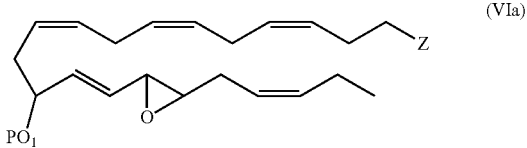

(VIa)

wherein $P_1$, Z, $R^a$, $R^b$, $R^c$, $R^d$, $R_1$ and n are as previously defined. In one aspect, $P_1$ is a hydrogen atom.

It should be understood that compounds (VI) and (VIa) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (VI) and (VIa). Purified compounds include that when Z is —C(O)OR$^d$, then R$^d$ for Z is a hydrogen.

In another aspect, the present invention provides new and useful DHA analogues such as a compound comprising the formula (VII):

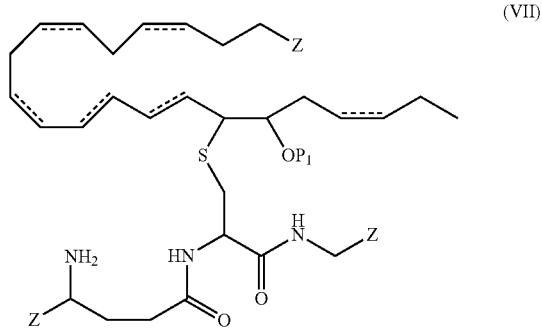

(VII)

wherein $P_1$, each Z independently, $R^a$, $R^b$, $R^c$, $R^d$ and n are as previously defined.

In one aspect, $P_1$ is a hydrogen atom. In another aspect, each Z is —C(O)OR$^d$ and R$^d$ of Z is a hydrogen atom. In another embodiment, the double bonds at the C-4/5, 7/8 and 19/20 positions are each of Z configuration.

In another aspect, the present invention provides new and useful DHA analogues such as a compound comprising the formula (VIIa):

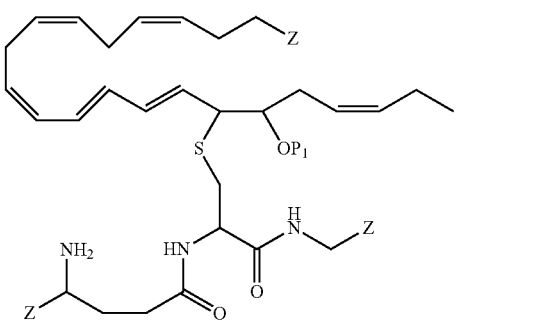

(VIIa)

wherein $P_1$, each Z independently, $R^a$, $R^b$, $R^c$, $R^d$, $R_1$ and n are as previously defined. In one aspect, $P_1$ is a hydrogen atom.

It should be understood that compounds (VII) and (VIIa) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (VII) and (VIIa). Purified compounds include that when Z is —C(O)OR$^d$, then R$^d$ for Z is a hydrogen.

In yet another aspect, the present invention provides new and useful DHA analogues such as a compound comprising formula (VIII):

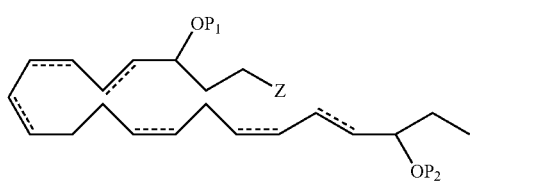

(VIII)

wherein $P_1$, $P_2$, -----, Z, $R^a$, $R^b$, $R^c$, $R^d$ and n are as previously defined, provided when Z is —C(O)OR$^d$, then R$^d$ for Z is not a hydrogen. In one embodiment, $P_1$ and $P_2$ are both hydrogen atoms. In one embodiment, the double bonds at C-7/8, 13/14 and 16/17 positions are each of Z configuration.

In still another aspect, the present invention provides new and useful DHA analogues such as a compound comprising the formula (VIIIa):

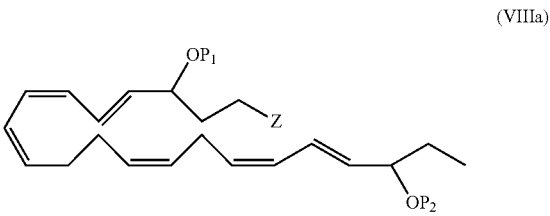

(VIIIa)

wherein $P_1$, $P_2$, -----, Z, $R^a$, $R^b$, $R^c$, $R^d$, $R_1$ and n are as previously defined. In one aspect, $P_1$ and $P_2$ are both hydrogen atoms.

It should be understood that compounds (VIII) and (VIIIa) include all pharmaceutically acceptable salts, esters thereof, the purified/isolated forms, as well as compounds wherein the hydroxyl is converted into a protecting group as described herein.

In another aspect, the present invention provides new and useful DHA analogues such as a purified compounds comprising the formulae (VIII) and (VIIIa). Purified compounds include that when Z is —C(O)OR$^d$, then R$^d$ for Z is a hydrogen.

In another embodiment, the hydrogen atom of the hydroxyl bearing carbon atom(s), e.g, at —OP$_1$ and/or OP$_2$ can be replaced with an alkyl group, such as a methyl group to help prevent oxidation for any of compounds I through VIIIa.

In another aspect, the present invention provides pharmaceutical compositions comprising one or more compounds of the invention, with or without other active pharmaceutical ingredients, in admixture with a pharmaceutically acceptable vehicle. Such a preparation can be administered according to the methods of the current invention.

It should be understood that the intermediates described herein are also included as part of the invention and can be considered active agents as well. For example, ketone containing intermediates are within the scope of the active agents as well as alkyne intermediates as described herein.

Results and Discussion

While AEA functions as a cannabinoid receptor agonist and its metabolism is well appreciated (12,14-16,27), the roles of DHEA and its metabolome are of interest since DHA treatment reduces traumatic brain injury (2) and is the precursor to potent proresolving mediators, including the resolvins and protectins (1,7,8). In the present study, HDHEA was identified in mouse brain, which provided the basis for further investigation of 17-HDHEA and 17-HpDHEA metabolic fates and potential biological impact of DHEA metabolism. Given the lack of functional groups for efficient ionization via electrospray ionization (ESI), direct analysis/detection of DHEA or its oxygenated metabolites with LC-MS-MS was impeded with low sensitivity. To this end, their acetate adducts, [M+CH$_3$COOH—H]$^-$, were targeted for analysis, which proved to be a useful alternative strategy employed in the present investigation. In terms of both detection limits and tandem mass fragmentation patterns, these oxygenated DHEA acetate adducts were comparable to those of the corresponding free acid-derived products.

Since AEA is a reported substrate for murine leukocyte type 12/15-LOX, reticulocyte type 15-LOX and soybean 15-LOX to generate 15-hydroperoxyarachidonoyl ethanolamide (18), it was rationalized 17-HDHEA as the reduced hydroxyl group containing product of 15-lipoxygenase-like-enzyme with DHEA. This hypothesis proved consistent with LC-MS-MS mass analysis of the reduced product obtained from incubation of DHEA with soy bean 15-LOX, which essentially showed the same LC retention time, tandem mass fragmentation patterns as well as online UV spectrum with endogenous 17-HDHEA (FIG. 1).

To determine 17-HpDHEA/17-HDHEA metabolic fates, LC-MS-MS-based lipidomic investigation led to identification of a series of novel oxygenated products listed in Table 1. Incubation of either 17-HpDHEA or DHEA with human PMN or mouse brain also gave a novel series of dioxygenated products, such as 4,17-diHDHEA, 7,17-diHDHEA, 10,17-diHDHEA, as well as 15-HEDPEA (Table 1). From DHA, some of these products are biosynthesized in inflammatory exudates, namely resolvin D5 (7,17-diHDHA) and resolvin D6 (4,17-diHDHA)(8) as well as the double dioxygenation product 10,17-diHDHA, an isomer of neuroprotectin D1 (6). Hence their ethanolamide counterparts were identified in the present study. In addition, incubation of 17-HpDHEA with hemoglobin generated two major hepoxilin-like structures (29), 13-HEDPEA and 15-HEDPEA. Given that hepoxilin diastereomer mixtures are generated from hemoglobin or hemin (29), it was of interest whether this was the case for 17-HpDHEA-derived compounds. To this end, NMR chemical shift of H-18 of isolated 13-HEDPEA displayed two distinguishable peaks at 4.23 ppm and 4.45 ppm, and chemical shift of H-13 of isolated 13-HEDPEA showed broad peaks around 3.9 ppm (Supplemental Table 2a and 2b), which strongly suggested the presence of diastereomers. In order to determine the biosynthetic mechanism of formation of 13-HEDPEA and 15-HEDPEA from hemoglobin and 17-HpDHEA, incubations were also carried out in $^{18}$O water. Tandem mass analysis of these incubation products indicated that $^{18}$O was not incorporated within these products (data not shown), which suggested the oxygen source of hydroxyl group could be attributed to atmospheric $O_2$.

TABLE 1

Structures, LC-MS and GC-MS fragmentations, and UV λmax for novel DHEA metabolites identified using mediator-based lipidomics

| Structure[†] | Trivial Name | LC retention time (min) | LC-MS major/ diagnostic fragment ions (m/z) | UV λ max (nm) | PMN + DHEA or HpDHEA | Hgb + HpDHEA | Mouse brain + DHEA |
|---|---|---|---|---|---|---|---|
| (structure) | 17-HDHEA | 26.6 | 446 (M + AcOH − H), 386(M − H), 368, 317, 288, 281, 201. | 237 | yes | yes | yes |
| (structure) | 4,17-diHDHEA | 20.6 | 462 (M + AcOH − H), 402(M − H), 384, 366, 333, 315, 304, 286, 257, 239, 144 | 238 | yes | not detected | yes |
| (structure) | 7,17-diHDHEA | 18.2 | 462 (M + AcOH − H), 402(M − H), 384, 366, 304, 286, 184, 156. | 246 | yes | not detected | trace |

TABLE 1-continued

Structures, LC-MS and GC-MS fragmentations, and UV λmax for novel DHEA metabolites identified using mediator-based lipidomics

| Structure[†] | Trivial Name | LC retention time (min) | LC-MS major/ diagnostic fragment ions (m/z) | UV λ max (nm) | PMN + DHEA or HpDHEA | Hgb + HpDHEA | Mouse brain + DHEA |
|---|---|---|---|---|---|---|---|
| | 10,17-diHDHEA | 17.7 | 462 (M + AcOH − H), 402(M − H), 384, 366, 304, 196. | 270 | yes | not detected | trace |
| | 15-HEDPEA | 21.3 | 462 (M + AcOH − H), 402(M − H), 384, 366, 315, 304, 286, 262. | conjugated double bond system not present | yes | not detected | minor, no clear mass spectrum |

[†]Stereochemistries shown are tentative assignments.

Figure 6:
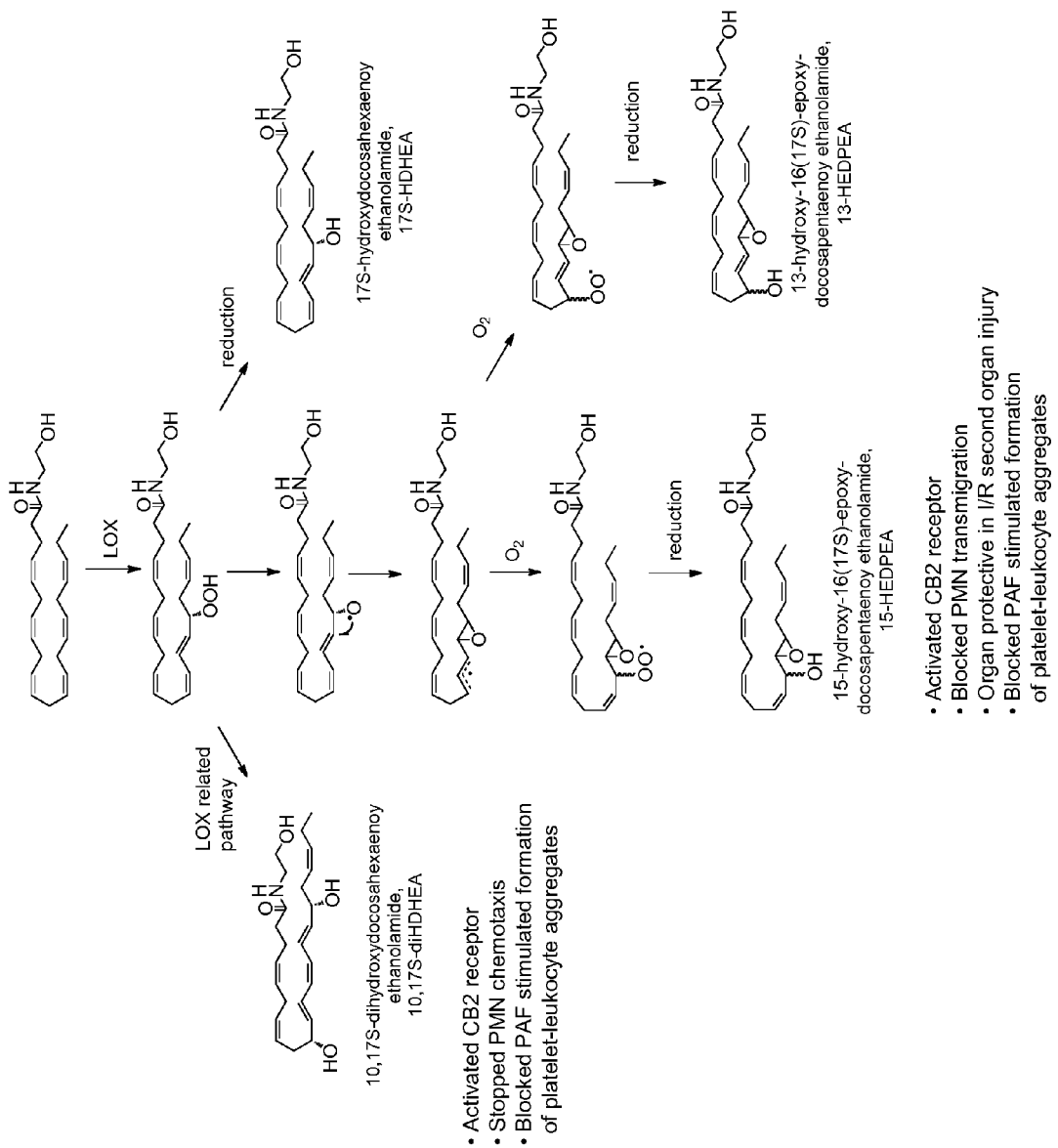
FIG. 6. Proposed DHEA metabolome and bioactive products.

Combining results from lipodomic analyses and the mechanisms proposed for phytooxylipin and hepoxilin biosynthesis (30), the pathways for novel oxygenated DHEA products are proposed in FIG. 6. In this scheme, DIVA is first converted to 17-HpDHEA mediated by 15-LOX. Then 17-HpDHEA is partially reduced to the oxide radical (FIG. 6) by hemoglobin, which reacts with vicinal double bond at 16-position to yield 16(17)-epoxide radical. Non- or low-stereospecific addition of oxygen to intermediate leads to formation of two types of peroxide radical diastereomers. Further reduction can generate 13-HEDPEA and 15-HEDPEA. Alternatively, 17-HpDHEA can undergo reduction to yield 17-HDHEA. Of interest, hemoglobin interactions with 17-HpDHEA yield approximately equal amount of 13-HEDPEA and 15-HEDPEA; for comparison, incubation of PMN with DHEA or HpDHEA generated predominantly 15-HEDPEA (Table 1 and Supplemental Table 1), suggesting the presence of a distinct 15-HEDPEA synthase in human PMN.

In view of the requirement for methodology development for functional screening to keep up with the rapid expansion of modern metabolomics, microfluidic chambers were coupled in tandem for screening chemotactic activity of human PMN with the novel DHEA derived products. Given the ~1 μl volume of the assay chamber, only small amounts of materials were required for these analyses. Results from the screening reported in FIG. 3 indicated that 15-HEDPEA (10 nM) effectively stopped PMN chemotaxis stimulated with IL-8 gradient. Microfluidic chamber-based screening of human PMN chemotaxis offers several advantages that include: a) the small amounts needed in the ~1 μl$^3$ chamber, b) the system permits capture of human leukocytes in less than five minutes compared to several hours (2-3) of isolation using density gradient, and c) video documentation of single PMN responses (9). Hence, the present results further demonstrate microfluidic chamber-based functional screening as an effective novel approach to decode rare and transient functional metabolites.

AEA exerts a wide range of functions via binding to CB receptors (14-17). However, its DHA metabolite DHEA displays only moderate affinity to CB1 receptor (Ki 324 nM vs. 40 nM for AEA) (31). To investigate the biological implications of DHEA metabolic oxidation in terms of activating CB receptors, two of the major PMN products were assessed, 10,17-diHDHEA and 15-HEDPEA, using CB2-beta arrestin ligand systems. The $EC_{50}$ for the novel DHEA-derived products, 10,17-diHDHEA and 15-HEDPEA, were $3.9 \times 10^{-10}$ M and $1.0 \times 10^{-10}$ M respectively, similar to that of AEA (FIG. 4). For comparison, $EC_{50}$ for DHEA was $9.8 \times 10^{-9}$ M, approximately 2 orders of magnitude higher. 10,17-diHDHEA and 15-HEDPEA also activated CB1 as shown in FIG. 4a. Ligand-CB2 interactions were confirmed using the specific CB2 antagonist AM630 (FIG. 4e,f). Another molecular target of AEA are the vanilloid receptors (TRPV1) in addition to the cannabinoid receptors, which required micromolar range for activity (32). The results indicated that metabolic oxygenation of DHEA produces novel CB agonists with enhanced potencies that are in the nanomolar range.

Since the production of certain NAE is enhanced during stroke (33), it was of interest to investigate biological functions of DHEA and its metabolites in platelet-leukocyte aggregate formation in human whole blood. Platelet-leukocyte aggregate formation is a component of many vascular diseases, stroke, diabetes, and hypertension (28). Specifically, increased platelet-leukocyte aggregates were suggested as an early marker for acute myocardial infarction and is increasingly regarded as a cardiovascular risk factor (34). Also patients with elevated circulating platelet-monocyte aggregates may reflect a pro-atherogenic phenotype (35). The presence of platelet-leukocyte aggregates stimulate production of pro-inflammatory cytokines, such as IL-1β, IL-8, MCP-1, MIP-1b, PAF and matrix metalloproteinase, as well as pro-coagulant tissue factors (for recent review see (28)). For these reasons, the formation of platelet-leukocyte aggregates is targeted for the therapeutic intervention (for reviews see (28,36)). The lipidomics investigation indicated that 10,17-diHDHEA and 15-HEDPEA were two major DHEA-derived products produced by isolated human PMN. Thus the actions of these compounds were assessed in PAF stimulated platelet-leukocyte aggregate formation, Both 10,17-diHDHEA and 15-HEDPEA were potent signals and, at concentrations as low as 10 pM, each decreased 100 nM PAF stimulated platelet-monocyte aggregate formation ~30% in human whole blood (FIG. 5a). The 10,17-diHDHEA also decreased PAF stimulated platelet-PMN aggregates by 25%-35% (FIG. 5b). For comparison, the precursor DHEA did not significantly inhibit formation of platelet-leukocyte aggregates within this dose range (FIGS. 5a and 5b).

Formation of platelet-leukocyte aggregates depends mostly on the activation of platelets (37). Along these lines, 10,17-diHDHEA (10 pM to 100 nM) blocked P-selectin surface expression of PAF stimulated platelets (FIG. 5c), suggesting that 10,17-diHDHEA actions were at least partially achieved via reductions in P-selectin mobilization and surface appearance-related platelet activation. The present results demonstrate that DHEA metabolic oxygenation generated potent molecules that reduce platelet activation and platelet-leukocyte aggregate formation in human whole blood.

Ischemia/reperfusion or reflow injury is the major cause of organ injury post-myocardial infarction, stroke, surgery, and organ transplantation injury and involves platelet and PMN activation (24). In this setting, neutrophils play critical roles in initiation of reperfusion or reflow injury and in consequent tissue damage. Hence, prevention of PMN activation or accumulation in ischemia organ reduces tissue injury after reperfusion (24,38). The present results obtained from chemotaxis screening might serve as useful benchmarks for searching/selecting potential protective mediators for ischemia/reperfusion injury. In this regard, 15-HEDPEA, which effectively stopped PMN chemotactic migration, was next evaluated in the mouse ischemia/reperfusion second organ injury initiated by hind limb occlusion. Indeed, 15-HEDPEA at 1 µg/mouse was organ protective, decreasing PMN infiltration in lung by ~50%. It is noteworthy that aberrant and excessive leukocytic infiltration is also associated with other diseases, including arthritis and psoriasis (39,40). Of interest, Kim et al. recently reported that DHEA promotes development of hippocampal neurons (41).

In summation, lipidomic investigation of DHEA functional metabolome uncovered a series of novel oxygenated products that 1) are potent CB2 agonists, 2) regulate single-cell PMN chemotactic responses, 3) modulate platelet-leukocyte interaction in whole blood, and 4) are organ protective. In view of the role of lipid mediators in inflammation and its resolution as well as hemostasis (7), the present new DHEA metabolome documented herein may serve as a counter-regulatory system in neural tissues and those rich in DHEA as well as in administration of DHA (42) to regulate leukocyte-mediated tissue damage.

Materials and Methods

Materials—

LC grade solvents were purchased from Fisher Scientific (Pittsburgh, Pa.). Phenomenex Luna C18 (150 mm×2 mm×5 µm) column and Strata-X solid phase extraction columns were purchased from Phenomenex (Torrance, Calif.). Soybean lipoxygenase, human hemoglobin, human serum albumin (HSA), d-4 MeOH, Hanks' balanced salt buffer (HBSS) were purchased from Sigma-Aldrich (Milwaukee, Wis.). N,O-bis-(trimethylsilyl)-trifluoroacetamide (BSTFA) was purchased from Pierce (Rockford, Ill.), P-selectin was purchased from R&D Systems (Minneapolis, Minn.). PE-conjugated mouse anti-human CD62P and FITC-CD41 anti-human were purchased from BD Biosciences (Rockville, Md.). FITC-conjugated mouse anti-human CD14, mouse anti-human CD16, Cy5-conjugated mouse anti-human CD3, and mouse anti-human CD20 were all purchased from Pharmingen (San Jose, Calif.). 17-HDHA standard was prepared from DHA and soybean lipoxygenase (8,19). Docosahexaenoyl ethanolamide (DHEA) was custom synthesized by Dr. Piomelli's group at UC-Irvine or purchased, as was 15(S)-HETE ethanolamide (15(S)-HAEA)) from Cayman Chemical (Ann Arbor, Mich.).

Animals—

All animals used in the present study were male FVB mice (Charles River Laboratories) that were 6-8 wk-old (weighing 20-25 g). They were maintained in a temperature and light-controlled environment, and had unlimited access to water and food (laboratory standard rodent diet 5001 (Lab Diet)), containing 1.5% EPA, 1.9% DHA of total fatty acids. Experiments were performed in accordance with the Harvard Medical School Standing Committee on Animals guidelines for animal care (Protocol 02570).

RP-HPLC—

Liquid chromatographic analyses and separations were performed using an Agilent 1100 series high performance liquid chromatography (HPLC) system (Agilent, Santa Clara, Calif.) equipped with G1379A degasser, G1312A binpump and G1315B UV diode array detector. HPLC analyses were carried out using a Phenomenex C18 column (150 mm×2 mm×5 pun) with the mobile phase of 0.2 ml/min flow rate (methanol:water, 70:30 v/v from 0 to 18 min, then ramped to 100% methanol from 18 to 35 min). Compound isolations/purifications were carried out using a Beckman ODS column (10 mm×250 mm×5 µm) with the mobile phase flow rate at 4 ml/min (methanol:water, 70:30 v/v from 0 to 18 min, then ramped to 100% methanol from 18 to 35 min).

Lipidomics MS-MS Analysis—

Sample analyses were carried out using a mass spectrometer (Qstar XL quadrupole TOF hybrid mass spectrometer (Applied Biosystems, Foster City, Calif.) equipped with two Shimazu LC20AD HPLC pumps (Shimazu, Columbia, Md.) and Agilent G1315B UV diode array detector (Agilent, Santa Clara, Calif.). For routine analyses, samples were extracted using C-18 cartridge as in (19) and injected to a Phenomenex C18 column (150 mm×2 mm×5 µm), and the mobile phase (methanol:water; 70:30 v/v from 0 to 18 min, then ramped to 100% methanol from 18 to 35 min) was eluted at a 0.2 ml/min flow rate and UV detector scanned from 200 to 400 nm before samples entered the MS-MS. GC-MS analysis was carried out as in (9). Samples were injected in 2.5 µL hexane.

Preparation of Oxygenated DHEA Products—

DHEA (12.5 mg) was suspended in 0.05 M borate buffer (250 ml, pH=9.3) at 4° C., and 160 kilounits soybean LOX (type VI, 640 kilounits total, 701 kilounits/mg protein, 3.6 mg of protein/ml) was added at 0, 2, 4, and 6 min. The incubation was monitored using UV spectrometer (Agilent, Santa Clara, Calif.). Incubations were treated with $NaBH_4$ before extraction two times with 200 ml ether. The organic layers were combined, washed twice with 100 ml dd-$H_2O$, taken to dryness under nitrogen flow, and subjected to preparative HPLC isolation monitoring online UV at 235 nm, 245 nm, and 270 nm, for isolation of 4,17-diHDHEA, 7,17-diHDHEA, and 14,17-diHDHEA respectively. The corresponding fraction was collected, dried under nitrogen and resuspended in methanol. Preparation of each compound was confirmed using GC-MS or LC-MS-MS before further investigation.

Preparation of HEDPEA—

Human hemoglobin (400 mg) was added to 17-HpDHEA (2.75 mg) suspended in 25 ml phosphate buffer (0.1 M, pH 7.3, 37° C.) and vortexed (5 min). The incubations were carried out at 37° C. for 6 min, and then diluted with dd$H_2O$ to 100 ml and extracted twice with 150 ml ether. The organic layer was combined and washed twice with 100 ml dd-$H_2O$. The crude product was taken to dryness under nitrogen flow and then isolated by preparative HPLC isolation. The fractions were isolated and collected monitoring UV absorbance at 215 nm. Each fraction was collected, taken to dryness under nitrogen flow, subjected to LC-MS-MS and/or NMR analysis, or derivatized with BSTFA and then subjected to GC-MS analysis.

Receptor-Ligand Interactions—

Receptor activation with the CB2 beta arrestin system was carried out essentially as in (20,21). HEK cells stably overexpressing human CB2 receptor tagged with Pro-Link and EA labeled beta-arrestin (Discoverx, Fremont Calif.) were plated at 20,000 cells/well of a 96 well plate. Forty-eight hours post plating, cells were incubated with compounds at concentrations from 1 pM to 100 nM for 1 h in serum free DMEM at 37° C. Ligand receptor interaction was determined by measuring chemiluminescence using the Pathhunter EFC detection kit (Discoverx, Fremont, Calif.), generated upon coupling of the EA labeled beta arrestin with the Pro-Link tagged receptor, with a plate reader (Envision, Perkin Elmer, Santa Clara, Calif.).

PMN Isolation and Incubations—

Human whole blood was collected (Brigham and Women's Hospital protocol 88-02642) and PMNs were isolated as in refs. (8,9,11). PMNs ($2\times10^6$) suspended in 1 ml DPBS+/+ with 0.2% bovine serum albumin (Sigma) were incubated with 5 µg of HPLC isolated 17-HpDHEA or DHEA, alone or with Zymosan A (100 µg/m) for 30 min at 37° C., and incubations were stopped with 2 volumes of ice-cold methanol. The mixture was kept in −20° C. for at least 2 h to precipitate proteins, and then taken for C18 solid phase extraction and analysis.

Leukocytic Chemotaxis Screening of DHEA Metabolites with Microfluidic Chamber—

The fabrication and surface modification of the microfluidic devices were prepared as in refs. (9,22). Whole blood (5-10 µl) diluted in HBSS (1:10, v/v) was introduced into the chemotaxis chamber via a cell inlet and neutrophils were captured along the chamber via P-selectin tethering. Next, the transversal gradient of IL-8 (0-10 nM) was introduced to the chemotaxis chamber. After fifteen minutes, novel DHEA metabolites (at a uniform concentration) were introduced to the chemotaxis chamber from the second gradient generator network, and 10 nM IL-8 gradient was maintained Single-cell neutrophil chemotaxis was recorded using microscopy (Nikon, Eclipse E600) equipped with a video camera (Diagnostic, RT Slider) and subject to analysis using ImageJ software (9).

PAF-Stimulated Platelet-Leukocyte Aggregate Formation—

Whole blood was incubated with either vehicle, HPLC isolated 10,17-diHDHEA or 15-HEDPEA (0.01-100 nM) for 15 min at 37° C. with intermittent mixing. Vehicle or PAF (100 nM, PAF C-16, Cayman Chemical, Ann Arbor, Mich.) was added for another 30 min at 37° C. with intermittent mixing. Incubation was stopped by ice-cold red blood cell lysis buffer (10 min at 4° C.). Cells were collected using centrifugation (210 g, 5 min, 4° C.) then fixed with 3% formalin (15 min, 4° C.). Cells were stained with FITC-anti-human CD41 (1:100, v/v) and PE-anti-human-CD62P (1:100, v/v) for 20 min at 4° C., and were analyzed using a flow cytometry and Cell Quest software as in (23). Cellular composition within whole blood was determined by forward and side scattering as well as cell-specific markers, anti-human-CD41 for platelets, anti-human-CD14 for monocytes and anti-human-CD16 for neutrophils.

Second Organ Reperfusion Injury—

Murine hind limb vascular occlusion second organ lung reperfusion injury was performed using 6- to 8-week-old FVB male mice and carried out as in (24).

Statistical Analysis—

The significance of difference between groups was evaluated using the two-tailed Student's t-test. P values of less than 0.05 were considered to be statistically significant Results Functional Metabolomics a) LC-UV-MS-MS Identification of 17-HDHEA from Brain.

To investigate the potential endogenous generation of DHEA-derived bioactive products, mouse brain was harvested, subject to solid phase extraction (19), and resulting methyl formate fractions were taken for LC-UV-MS-MS-based metabolomics. Tandem mass fragmentations and online UV spectrum with characteristic $\lambda_{max}$ at 237 nm are consistent with the proposed structure as shown in the inset of FIG. 1. Because of the lack of suitable functional groups for direct efficient ionization and analysis of 17-hydroxy-4Z,7Z,10Z,13Z,15,19Z-docosahexamoylethanolamide (17-HDHEA), its acetate adduct m/z 446=[M+$CH_3COOH$—H] was targeted for analysis. The major tandem mass ions were assigned as following: m/z 386=[M-H], 368=[M-H−1120], 281=[299−$H_2O$]. The m/z 288 is consistent with fragmentation at Position 17 (see Table 1 for numbering) (FIG. 1b). Because of the limited quantities of endogenous 17-HDHEA produced in brain tissue, further analyses and in vitro enzymatic preparation were carried out by incubating DHEA with 15-LOX followed by reduction with $NaBH_4$ (see Methods). Endogenous 17-HDHEA and the enzymatically prepared compound in vitro gave essentially the same LC retention times and tandem mass fragmentations using LC-MS-MS (see Supplemental FIG. 1). To assess their production by human and mouse tissues, DHEA was also incubated with isolated human PMN or whole mouse brain because DHEA is enriched in this tissue. LC-MS-MS-based targeted lipidomics indicated the production of a novel series of oxygenated DHEA (Table 1).

b) Decoding Metabolomics Using Microfluidic Chambers.

In parallel to structure elucidation, chemotactic screening of HPLC isolated DHEA metabolites obtained from mouse brain was carried out utilizing microfluidic chamber (FIG. 1c). After IL-8 (0-10 nM gradient) was introduced to the main channel of the microfluidic device, P-selectin tethered leukocytes rapidly migrated along the IL-8 chemotactic gradient at an average rate of 2.3 µm/min. After 15 min, the mixture of metabolites was infused into the microfluidic main channel while an IL-8 (0-10 nM) gradient was maintained (FIG. 1c, left panel). Human PMN chemotaxis was dramatically reduced (p<0.01) upon the addition of the brain metabolite mixture, whereby average human PMN chemotaxis velocity dropped from 2.3 µm/min to ~0.7 µm/min (FIG. 1c, middle panel). This decrease in chemotaxic velocity was maintained even after the gradient was switched back to IL-8. These results indicated that the brain metabolites contained bioactive components that stopped PMN chemotaxis.

c) LC-UV-MS-MS and GC-MS-Based Metabolomics of DHEA.

Results from this screening uncovered that at least one bioactive product was present among the mixture of DHEA metabolites; thus, we pursued the metabolic fates of DHEA and 17-HpDHEA/17-HDHEA identified in mouse brain (FIG. 1b) using LC/UV/MS/MS-based lipidomics. As with 17-HDHEA, acetate adducts of potential DHEA derived metabolites [M+$CH_3COOH$—H] were targeted for tandem mass analysis (Table 1). These results demonstrated the presence and production of novel products in the DHEA metabolome.

Incubations of isolated human PMNs with DHEA or 17-HpDHEA led to the generation of 17-HDHEA, 4,17-diHDHEA, 10,17-diHDHEA and 15-HEDPEA. Human hemoglobin, which can be liberated upon tissue damage (25), was incubated with 17-HpDHEA, gave 13-HEDPEA and 15-HEDPEA as prominent products, as well as 17-HDHEA (Table 1). Mouse brain homogenates with DHEA also produced 17-HDHEA and 4,17-diHDHEA as major products with smaller amounts of 7,17-diHDHEA, 10,17-diHDHEA and 15-HEDPEA. The online UV and tandem mass spectra for 4,17-diHDHEA are shown in FIGS. 2$a$ and 2$b$. The adduct parent ion, analyte parent ion and the ions resulted from neutral loss are m/z 462=[M+CH$_3$COOH—H], 402=[M-H], 384=[M-H—H$_2$O], 366=[M-H–2H$_2$O], which are common signature ions for all dihydroxy-containing DHEA products. The ions m/z 333, 315=[333–H$_2$O], 304, 286=[304–H$_2$O] were assigned as diagnostic ions for fragmentations at Position 17. Fragmentations at Position 4 can lead to m/z 144, 257 and 239=[257–H$_2$O]. Its UV spectrum displayed characteristic maximum absorbance at 238 nm, which was consistent with the presence of two separated conjugated diene structures in this compound. As shown in FIGS. 2$c$ and 2$d$, diagnostic ions m/z 304, 286=[304–H$_2$O]; 184, 156, corresponded to the fragmentations at Positions 7 and 17 of 7,17-diHDHEA respectively (see Table 1 for numbering). The UV spectrum of the compound displayed maximum absorbance, $\lambda_{max}$, at 246 nm (26), consistent with the presence of two diene structures separated by a methylene group. For 10,17-diHDHEA, m/z 333, 315=[333–H$_2$O], 304, 286=[304–H$_2$O], 196 came from fragmentations at Positions 10 and 17 as shown in FIGS. 2$e$ and 2$f$. The presence of a conjugated triene structure in 10,17-diHDHEA was confirmed by the characteristic UV spectrum with $\lambda_{max}$ at 270 nm. Tandem mass spectrum of 13-HEDPEA is shown in Supplemental FIG. 2$a$ with signature fragmentation ions m/z 320, 304, 286=[304–H$_2$O], 236. GC/MS was also utilized for additional structural analysis with 13-HEDPEA and 15-HEDPEA that confirmed the original tandem MS assignments shown in Supplemental FIGS. 2$c$ and 2$d$. The C-value for 13-HEDPEA was determined as 32.1±0.2 (Supplemental FIG. 2$e$) and for 15-HEDPEA was 33.7±0.2 (Supplemental FIG. 2$f$).

In order to determine concentrations, as well as to further confirm structures, HPLC isolated 13-HEDPEA and 15-HEDPEA were characterized using proton NMR ($^1$H NMR). The chemical shift assignments are shown in Supplemental Tables 2a and 2b, respectively. For 15-HEDPEA, the proton at Position 15 (H-15) displayed two distinct chemical shifts, which will be discussed later. Because of limited amounts of materials and the lack of informative UV chromophores present in these compounds, NMR spectroscopy was also used for quantitation using 17-HDHA as an internal standard with known concentrations. The NMR quantitated compounds were then used as standards for HPLC quantitation monitoring UV chromatogram at 210 nm or LC-tandem mass profiling (see Methods for further details).

Human PMN Single Cell Chemotactic Functional Screening.

HPLC isolated dioxygenated DHEA products were individually screened for direct PMN actions using microfluidic chambers. Infusion of isolated 15-HEDPEA at 10 nM to the main channel stimulated changes in morphology and chemotaxis of PMN in the IL-8 gradient and stopped further PMN migration after ~4 min (FIG. 3$a$). For direct comparison, PMN chemotaxis velocity did not change with time with the IL-8 gradient (Supplemental FIG. 3$a$). At 10 nM, 4,17-diHDHEA (FIG. 3$b$), 7,17-diHDHEA or 10,17-diHDHEA did not significantly regulate chemotaxis (Supplemental FIG. 3$b,c$), while at higher concentrations, e.g. 10 μM, 10,17-diHDHEA rapidly stopped PMN chemotaxis (FIG. 3$c$). These results indicate that 15-HEDPEA is the most potent of this series in regulating human PMN shape change and motility.

Cannabinoid (CB) Receptor Activation.

Since AEA exerts a wide range of bioactions via activating cannabinoid receptor(s) (14,27), It was next tested whether DHEA, 10,17-diHDHEA or 15-HEDPEA also activated CB receptors. To this end, recombinant human CB receptors were overexpressed in a beta-arrestin system as described in Experimental Procedures. AEA was used for direct comparison as a known agonist. FIG. 4 shows the dose response of CB 1 and 2 with each compound. Activation of CB2 by AEA gave $EC_{50}$~$1.1\times10^{-10}$ M and DHEA $9.8\times10^{-9}$ M. For comparison, $EC_{50}$ for metabolically oxygenated products, 10,17-diHDHEA and 15-HEDPEA, were $3.9\times10^{-10}$ M and $1.0\times10^{-10}$ M respectively. These results demonstrate enzymatic oxidation products from DHEA are activators of CB2 receptors, and that 10,17-diHDHEA and 15-HEDPEA also activated CB1 receptors but required much higher concentrations (FIG. 4$a$). By comparison, 15(S)-HAEA, the oxygenated product of AEA, did not stimulate CB2 receptors in this dose range. CB2 receptor-ligand interactions were confirmed with dose response of CB2 specific antagonist AM630. When incubated with GPCR CB2 over-expressed cells, AM630 inhibited activation stimulated with 15-HEDPEA (10 nM) and AEA (10 nM), used here for a known positive and direct comparison (FIGS. 4$e$ and 4$f$). AM630 also inhibited GPCR CB2 interaction with 10,17-diHDHEA at higher concentration (n=3, data not shown).

DHEA Products Reduced Platelet-Leukocyte Aggregate Formation in Human Whole Blood.

Figure 5:
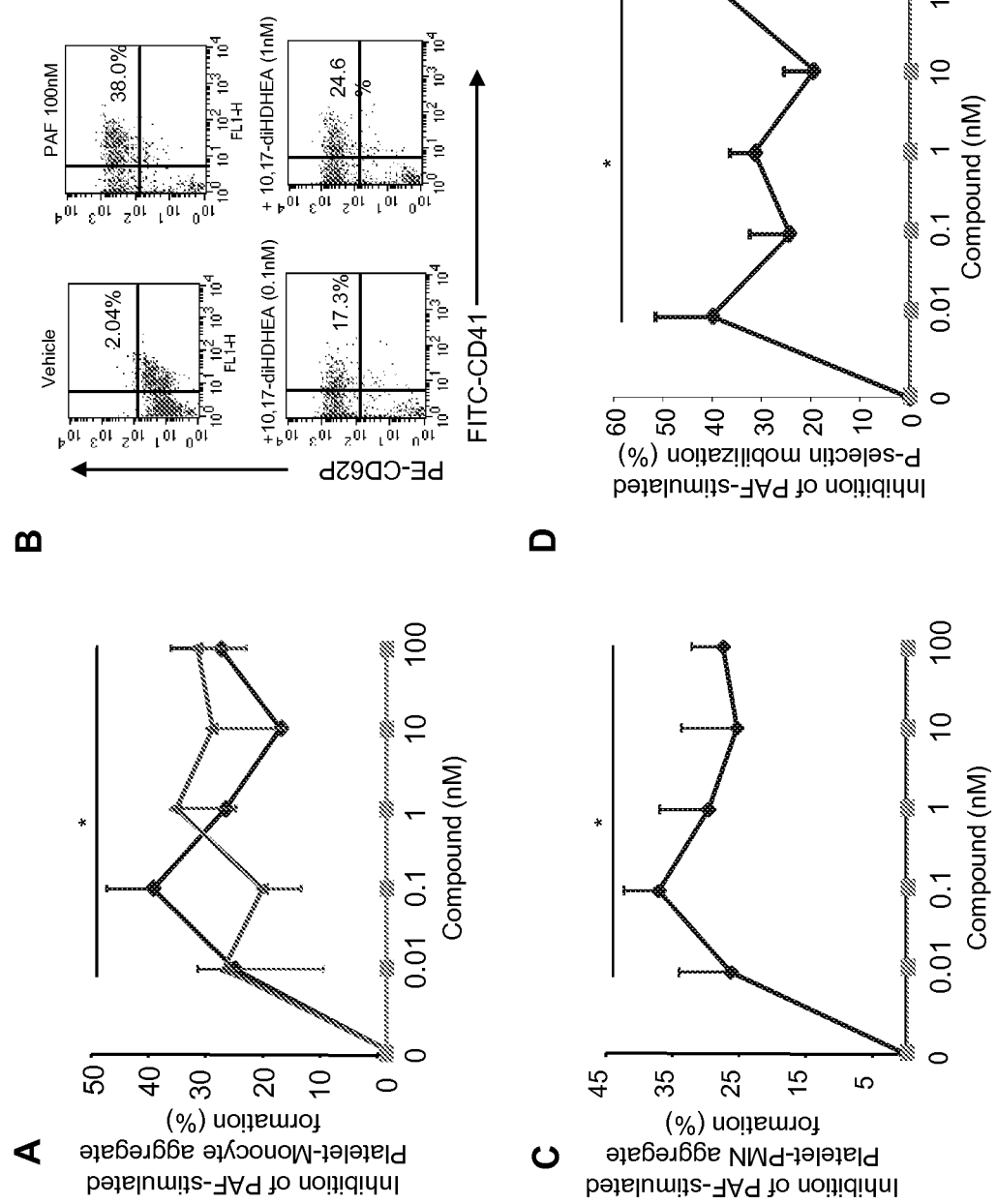
FIG. 5. In human whole blood, 10,17S-diHDHEA and 15-HEDPEA each block PAF-stimulated platelet-leukocyte aggregate formation. Human whole blood stimulated with PAF (100 nM) was incubated with 10,17-diHDHEA, 15-HEDPEA or DHEA for 30 min, 37° C. The incubation was stopped via ice-cold RBC lysis buffer. The majority of RBCs were removed and remaining cells were labeled. Platelet-leukocyte aggregate formation or P-selectin mobilization was analyzed using FACS (see Methods). Dose response inhibition of a) platelet-monocyte aggregate formation, b) representative dot plot of platelet-monocyte aggregates, c) platelet-PMN aggregate formation, d) platelet P-selectin mobilization, with indicated products. (diamonds 10,17-diHDHEA; triangles 15-HEDPEA; squares DHEA). Results are mean±SEM of n=5-6 donors. P<0.05 compared to vehicle treatment.

Platelet-leukocyte interactions play important roles in hemostasis, thrombosis, and inflammation (for recent review see (28) and references within). At concentrations as low as 10 pM, 10,17S-diHDHEA or 15-HEDPEA decreased PAF-(100 nM) stimulated platelet-monocyte aggregate formation in human whole blood by ~30% (FIG. 5$a,b$). The inhibitory action of 10,17-diHDHEA displayed a bell-shaped dose response and reached maximum reduction at ~40% with 100 pM. Formation of PMN-platelet aggregates with PAF (100 nM) was also inhibited by 10,17-diHDEA at concentrations as low as 10 pM, as was the surface expression of P-selectin on platelets in whole blood (FIG. 5$d$). By comparison, the precursor DHEA (unoxidized) was not active in this dose range (FIG. 5$a,b$).

Organ Protection in Ischemia/Reperfusion Injury.

Since 15-HEDPEA displayed potent bioactions with human PMN at single cell level (FIG. 3) and in human whole blood (FIG. 5), it was next questioned whether it had protective actions in vivo in murine hind limb ischemia (1 h) and second organ reperfusion (2 h) injury (24). Indeed, following reperfusion, 15-HEDPEA significantly reduced lung PMN accumulation in mice and associated lung injury at 1 μg/mouse, (Supplemental FIG. 4) (~50% reduction compared to vehicle; P<0.05).

Supplemental Information

SUPPLEMENTAL TABLE 1

Structures, LC-MS and GC-MS fragmentations, and UV λmax for novel DHEA metabolites identified using mediator-based lipidomics.
Supplemental Table 1. Structures, LC-MS and GC-MS fragmentations, and UV λmax for novel DHEA metabolites identified using mediator-based lipidomics.

| Structure[†] | Trivial Name | LC retention time (min) | LC-MS major/diagnostic fragment ions (m/z) | UV λ max (nm) | PMN + DHEA or HpDHEA | Hgb + HpDHEA | Mouse brain + DHEA |
|---|---|---|---|---|---|---|---|
| (structure) | 13-HEDPEA | 20.0 | 462 (M + AcOH − H), 402(M − H), 384, 366, 320, 304, 286, 236. | no conjugated system identified | trace | yes | not detected |
| (structure) | 16-GS-17-HDHEA | | 691(M − H), 673, 359, 562, 306, 272, 254. | 278 | PMN with HpDHEA and GSH | | |
| (structure) | 4,20-diHDHEA | | 462 (M + AcOH− H), 402(M − H), 384, 366, 257, 239, 144. | 236 | A major product of incubation of mouse brain and DHEA | | |

[†]Stereochemistries are tentatively assigned and the action of these products will be reported separately.

SUPPLEMENTAL TABLE 2a

NMR assignments of 15-hydroxy-16(17)-epoxy-DHEA.

| Proton position | δ(mult, J/Hz) |
|---|---|
| H-1 | 3.59 (t, J = 5.8) |
| H-2 | 3.28 (t, J = 5.8) |
| H-5 | 2.25 (t, J = 7.50) |
| H-6 | 2.38 (m) |
| H-7, H-8, H-10, H-11, H-13, H-14, H-22, H-23 | 5.3-5.5 (m) |
| H-9, H-12, H-15, H-19, H-20, H-21, | 2.80-2.95 (m) |
| H-16, H-17 | 5.50-5.60 (m) |
| H-18 | 4.23 (m) and 4.45(m) |
| H-24 | 4.45 (m) |
| H-25 | 0.96 (td, J = 7.4, 1.4) |

SUPPLEMENTAL TABLE 2b

NMR assignments of 13-hydroxy-16(17)-epoxy-docosapentaenyolethanolamide.

| Proton position | δ(mult, J/Hz) |
|---|---|
| H-1 | 3.58 (t, 5.9) |
| H-2 | 3.28 (t, 5.8) |
| H-5 | 2.25 (t, 7.2) |
| H-6, H-9, H-12 | 2.35 (m) |
| H-7, 11-8, H-10, H-11, H-13, H-14, H-22, H-23 | 5.35-5.50 (m) |
| H-16 | 3.9 (m) |
| H-17 | 5.58 (m) |
| H-18 | 5.95 (dd, 15.5, 5.7) |
| H-19 | 3.19 |

SUPPLEMENTAL TABLE 2b-continued

NMR assignments of 13-hydroxy-16(17)-epoxy-docosapentaenyolethanolamide.

| Proton position | δ(mult, J/Hz) |
|---|---|
| H-20, H-21 | 2.08 (m) |
| H-24 | 2.08 (m) |
| H-25 | 0.97 (t, 7.5) |

REFERENCES

1. Amason, B. G. (ed). (2010) *The Brain and Host Defense*, Elsevier, San Diego;
2. Bailes, J. E., and Mills, J. D. (2010) *J. Neurotrauma* 27, 1617-1624;
3. Marcheselli, V. L., Hong, S., Lukiw, W. J., Hua Tian, X., Gronert, K., Musto, A., Hardy, M., Gimenez, J. M., Chiang, N., Serhan, C. N., and Bazan, N. G. (2003) *J Biol Chem* 278, 43807-43817;
4. Yanes, O., Clark, J., Wong, D. M., Patti, G. G., Sánchez-Ruiz, A., Benton, H. P., Trauger, S. A., Desponts, C., Ding, S., and Siuzdak, G. (2010) *Nat Chem Biol* 6(6), 411-417;
5. Hassan, I. R., and Gronert, K. (2009) *J Immunol* 182, 3223-3232;
6. Bazan, N. G., Calandria, J. M., and Serhan, C. N. (2010) *J Lipid Res* 51, 2018-2031;
7. Serhan, C. N., Chiang, N., and Van Dyke, T. E. (2008) *Nat Rev Immunol* 8, 249-261;
8. Serhan, C. N., Hong, S., Gronert, K., Colgan, S. P., Devchand, P. R., Mirick, G., and Moussignac, R.-L. (2002) *J Exp Med* 196, 1025-1037;
9. Kasuga, K., Yang, R., Porter, T. F., Agrawal, N., Petasis, N. A., Irimia, D., Toner, M., and Serhan, C. N. (2008) *J Immunol* 181, 8677-8687;
10. Xu, Z.-Z., Zhang, L., Liu, T., Park, J.-Y., Berta, T., Yang, R., Serhan, C. N., and Ji, R.-R. (2010) *Nat Med* 16, 592-597;
11. Spite, M., Norling, L. V., Summers, L., Yang, R., Cooper, D., Petasis, N. A., Flower, R. J., Perretti, M., and Serhan, C. N. (2009) *Nature* 461, 1287-1291;
12. De Petrocellis, L., Melck, D., Bisogno, T., and Di Marzo, V. (2000) *Chem Phys Lipids* 108, 191-209;
13. Berger, A., Crozier, G., Bisogno, T., Cavaliere, P., Innis, S., and Di Marzo, V. (2001) *Proc Natl Acad Sci USA* 98, 6402-6406;
14. Devane, W. A., Hanus, L., Breuer, A., Pertwee, R. G., Stevenson, L. A., Griffin, G., Gibson, D., Mandelbaum, A., Etinger, A., and Mechoulam, R. (1992) *Science* 258, 1946-1949;
15. Di Marzo, V., Melck, D., Bisogno, T., and De Petrocellis, L. (1998) *Trends Neurosci* 21, 521-528;
16. Kozak, K., and Marnett, L. (2002) *Prostaglandins Leukot Essent Fatty Acids* 66, 211-220;
17. Pavlopoulos, S., Thakur, G. A., Nikas, S. P., and Makriyannis, A. (2006) *Curr Pharm Des* 12, 1751-1769;
18. Ueda, N., Yamamoto, K., Yamamoto, S., Tokunaga, T., Shirakawa, E., Shinkai, H., Ogawa, M., Sato, T., Kudo, I., Inoue, K., Takizawa, H., Nagano, T., Hirobe, M., Matsuki, N., and Saito, H. (1995) *Biochim Biophys Acta* 1254, 127-134;
19. Yang, R., Chiang, N., Oh, S. F., and Serhan, C. N. (2011) *Curr Protoc Immunol*, in press;
20. Olson, K. R., and Eglen, R. M. (2007) *Assay Drug Dev Technol* 5(1), 137-144;
21. Krishnamoorthy, S., Recchiuti, A., Chiang, N., Yacoubian, S., Lee, C.-H., Yang, R., Petasis, N. A., and Serhan, C. N. (2010) *Proc Natl Acad Sci USA* 107, 1660-1665;
22. Irimia, D., Liu, S. Y., Tharp, W. G., Samadani, A., Toner, M., and Poznansky, M. C. (2006) *Lab Chip* 6(2), 191-198;
23. Dona, M., Fredman, G., Schwab, J. M., Chiang, N., Arita, M., Goodarzi, A., Cheng, G., von Andrian, U. H., and Serhan, C. N. (2008) *Blood* 112(3), 848-855;
24. Qiu, F.-H., Wada, K., Stahl, G. L., and Serhan, C. N. (2000) *Proc Natl Acad Sci USA* 97, 4267-4272;
25. Kumar, V., Fausto, N., Abbas, A. (2004) *Robbins and Cotran Pathologic Basis of Disease*, 7th Ed., Saunders Elsevier, Philadelphia;
26. Tjonahen, E., Oh, S. F., Siegelman, J., Elangovan, S., Percarpio, K. B., Hong, S., Arita, M., and Serhan, C. N. (2006) *Chem Biol* 13(11), 1193-1202;
27. Felder, C. C., Briley, E. M., Axelrod, J., Simpson, J. T., Mackie, K., and Devane, W. A. (1993) *Proc Natl Acad Sci USA* 90(16), 7656-7660;
28. van Gils, J. M., Zwaginga, J. J., and Hordijk, P. L. (2009) *J Leukoc Biol* 85(2), 195-204;
29. Pace-Asciak, C. R., Reynaud, D., Demin, P., and Nigam, S. (1999) *Adv Exp Med Biol* 447, 123-132;
30. Rowley, F. A., Kuhn, H., and Schewe, T. (eds). (1998) *Eicosanoids and Related Compounds in Plants and Animals*, Portland Press, London;
31. Sheskin, T., Hanus, L., Slager, J., Vogel, Z., and Mechoulam, R. (1997) *J Med Chem* 40(5), 659-667;
32. Zygmunt, P. M., Petersson, J., Andersson, D. A., Chuang, H., Sørgård, M., Di Marzo, V., Julius, D., and Högestätt, E. D. (1999) *Nature* 400, 452-457;
33. Franklin, A., Parmentier-Batteur, S., Walter, L., Greenberg, D. A., and Stella, N. (2003) *J Neurosci* 23(21), 7767-7775;
34. Furman, M. I., Barnard, M. R., Krueger, L. A., Fox, M. L., Shilale, E. A., Lessard, D. M., Marchese, P., Frelinger, A. L., 3rd, Goldberg, R. J., and Michelson, A. D. (2001) *J Am Coll Cardiol* 38(4), 1002-1006;
35. Sarma, J., Laan, C. A., Alam, S., Jha, A., Fox, K. A., and Dransfield, I. (2002) *Circulation* 105(18), 2166-2171;
36. Weyrich, A. S., and Zimmerman, G. A. (2004) *Trends Immunol* 25, 489-495;
37. Rinder, H. M., Bonan, J. L., Rinder, C. S., Ault, K. A., and Smith, B. R. (1991) *Blood* 78(7), 1730-1737;
38. Kilgore, K. S., Todd, R. F., and Lucchesi, B. R. (1999) *Reperfusion Injury*, Lippincott, Williams and Wilkins, Philadelphia;
39. Preissner, W. C., Schroder, J. M., and Christophers, E. (1983) *Br J Dermatol* 109(1), 1-8;
40. Nishiura, H., Shibuya, Y., Matsubara, S., Tanase, S., Kambara, T., and Yamamoto, T. (1996) *J Biol Chem* 271(2), 878-882;
41. Kim, H.-Y., Moon, H.-S., Cao, D., Lee, J., Kevala, K., Jun, S., Lovinger, D., Akbar, M., and Huang, B. X. (2011) *Biochem J*, Epub January 31; doi: 10.1042/BJ20102118;
42. Calder, P. C. (2010) *Proc Nutr Soc* 69, 565-573.

The inventions illustratively disclosed herein suitably may be practiced in the absence of any element which is not specifically disclosed herein. Additionally, the inventions illustratively disclosed herein may be practiced in the absence of any element disclosed herein.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A compound comprising one of the formulae selected from (I) through (VIIIa):

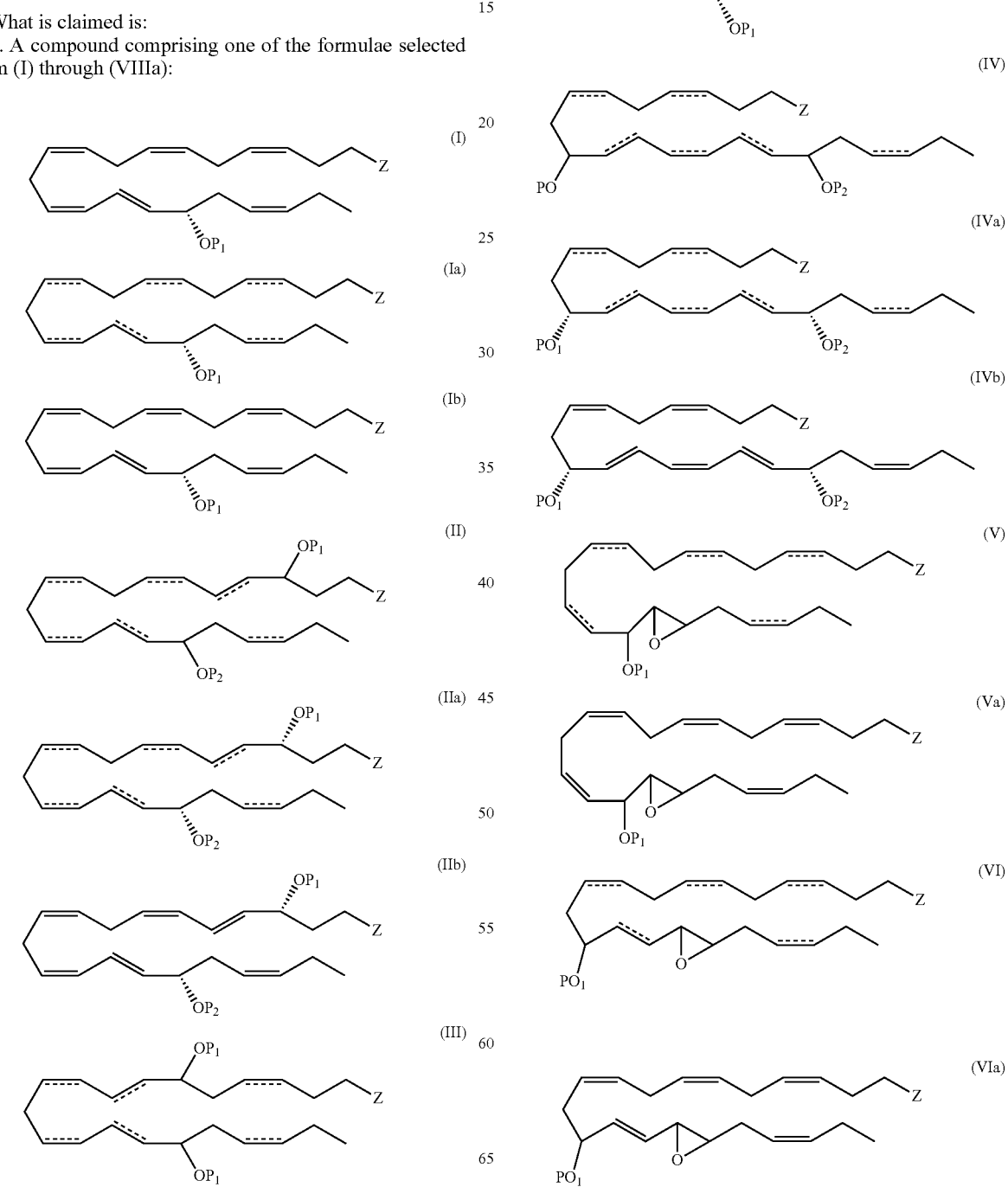

-continued (VII)

(VIIa)

(VIII)

(VIIIa)

wherein each of $P_1$ and $P_2$ individually, if present, is a protecting group or a hydrogen atom;
wherein ----- is a double bond if present;
wherein Z is —C(O)NR$^c$R$^c$, —C(O)NR$^c$R$^c$—OH, —C(NH)NR$^c$R$^c$ or —C(S)NR$^c$R$^c$;
each R$^a$, is independently hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;
each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally have one or more of the same or different additional heteroatoms and which may optionally be substituted with one or more of the same or different R$^a$ or suitable R$^b$ groups;
each R$^b$ is independently =O, —OR$^d$, (C1-C3) haloalkyloxy, —OCF$_3$, =S, —SR$^d$, =NR$^d$, =NOR$^d$, —NR$^c$R$^c$, halogen, —CF$_3$, —CN, —NC, —OCN, —SCN, —NO, —NO$_2$, =N$_2$, —N$_3$, —S(O)R$^d$, —S(O)$_2$R$^d$, —S(O)$_2$OR$^d$, —S(O)NR$^c$R$^c$, —S(O)$_2$NR$^c$R$^c$, —OS(O)R$^d$, —OS(O)$_2$R$^d$, —OS(O)$_2$OR$^d$, —OS(O)$_2$NR$^c$R$^c$, —C(O)R$^d$, —C(O)OR$^d$, —C(O)NR$^c$R$^c$, —C(NH)NR$^c$R$^c$, —C(NR$^a$)NR$^c$R$^c$, —C(NOH)R$^a$, —C(NOH)NR$^c$R$^c$, —OC(O)R$^d$, —OC(O)OR$^d$, —OC(O)NR$^c$R$^c$, —OC(NH)NR$^c$R$^c$, —OC(NR$^a$)NR$^c$R$^c$, —[NHC(O)]$_n$R$^d$, —[NR$^a$C(O)]$_n$R$^d$, —[NHC(O)]$_n$OR$^d$, —[NR$^a$C(O)]$_n$OR$^d$, —[NHC(O)]$_n$NR$^c$R$^c$, —[NR$^a$C(O)]$_n$NR$^c$R$^c$, —[NHC(NH)]$_n$NR$^c$R$^c$ or —[NR$^a$C(NR$^a$)]$_n$NR$^c$R$^c$;

each n, independently is an integer from 0 to 3; and each R$^d$, independently is a protecting group or R$^a$;

or a pharmaceutically acceptable salt thereof.

2. The compound of claim 1, wherein $P_1$ and $P_2$ are both hydrogen atoms.

3. The compound of claim 1, wherein Z is —C(O)NR$^c$R$^c$—OH.

4. The compound of claim 3, wherein one R$^c$ is H and the second R$^c$ is ethyl.

5. A purified compound comprising one of the formulae (I) through (VIIIa):

(I)

(Ia)

(Ib)

(II)

(IIa)

(IIb)

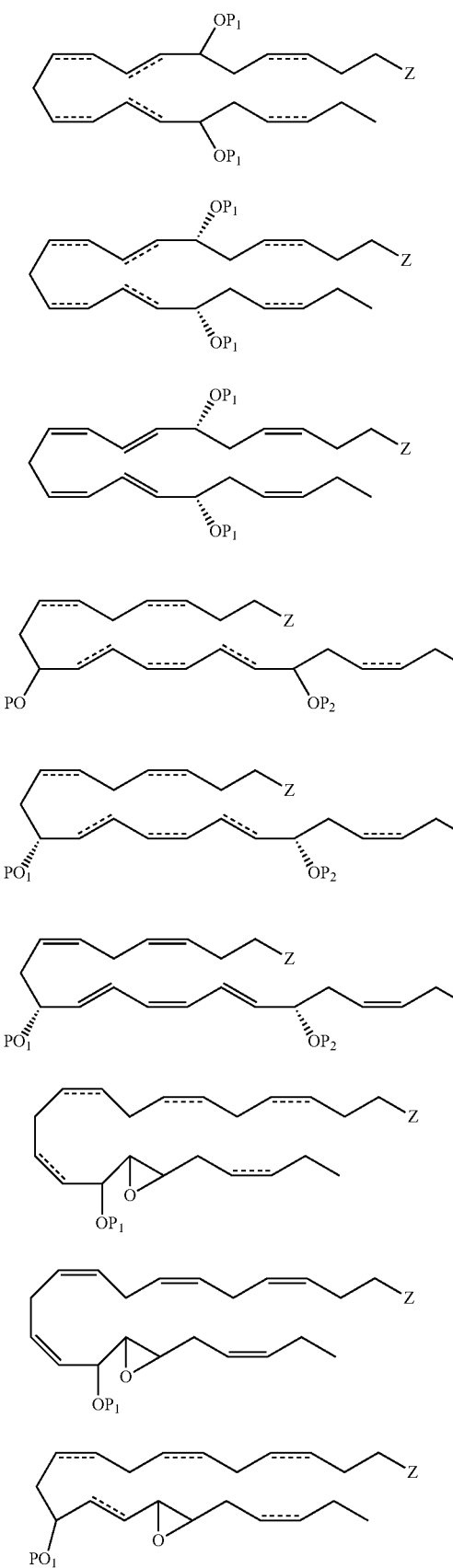
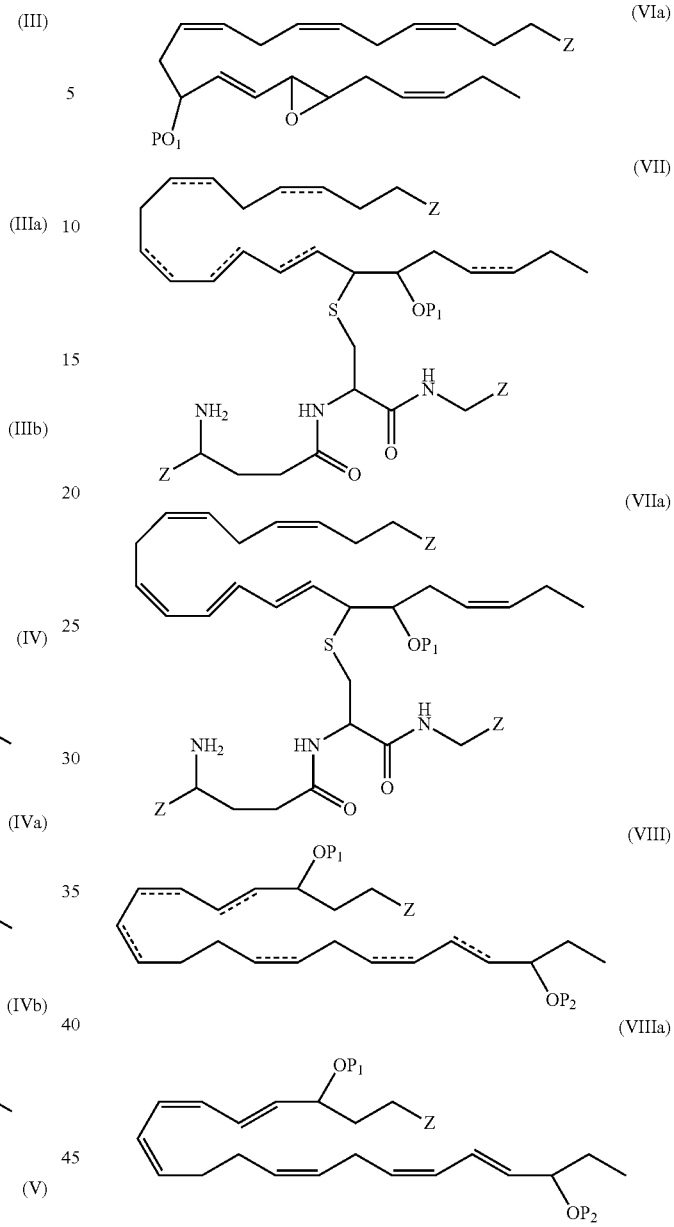

wherein each of $P_1$ and $P_2$ individually, if present is a protecting group or a hydrogen atom;

wherein ≈≈≈ is a double bond if present;

wherein Z is —C(O)NR$^c$R$^c$, —C(NH)NR$^c$R$^c$, or —C(S)NR$^c$R$^c$;

each R$^a$, is independently hydrogen, (C1-C6) alkyl, (C3-C8) cycloalkyl, cyclohexyl, (C4-C11) cycloalkylalkyl, (C5-C10) aryl, phenyl, (C6-C16) arylalkyl, benzyl, 2-6 membered heteroalkyl, 3-8 membered cycloheteroalkyl, morpholinyl, piperazinyl, homopiperazinyl, piperidinyl, 4-11 membered cycloheteroalkylalkyl, 5-10 membered heteroaryl or 6-16 membered heteroarylalkyl;

each R$^c$, is independently a protecting group or R$^a$, or, alternatively, each R$^c$ is taken together with the nitrogen atom to which it is bonded to form a 5 to 8-membered cycloheteroalkyl or heteroaryl which may optionally have one or more of the same or different additional heteroatoms and which may optionally be substituted with one or more of the same or different $R^a$ or suitable $R^b$ groups;

each $R^b$ is independently =O, —$OR^d$, (C1-C3) haloalkyloxy, —$OCF_3$, =S, —$SR^d$, =$NR^d$, =$NOR^d$, —$NR^cR^c$, halogen, —$CF_3$, —CN, —NC, —OCN, —SCN, —NO, —$NO_2$, =$N_2$, —$N_3$, —$S(O)R^d$, —$S(O)_2R^d$, —$S(O)_2OR^d$, —$S(O)NR^cR^c$, —$S(O)_2NR^cR^c$, —$OS(O)R^d$, —$OS(O)_2R^d$, —$OS(O)_2OR^d$, —$OS(O)_2NR^cR^c$, —$C(O)R^d$, —$C(O)OR^d$, —$C(O)NR^cR^c$, —$C(NH)NR^cR^c$, —$C(NR^a)NR^cR^c$, —$C(NOH)R^a$, —$C(NOH)NR^cR^c$, —$OC(O)R^d$, —$OC(O)OR^d$, —$OC(O)NR^cR^c$, —$OC(NH)NR^cR^c$, —$OC(NR^a)NR^cR^c$, —$[NHC(O)]_nR^d$, —$[NR^aC(O)]_nR^d$, —$[NHC(O)]_nOR^d$, —$[NR^aC(O)]_nOR^d$, —$[NHC(O)]_nNR^cR^c$, —$[NR^aC(O)]_nNR^cR^c$, —$[NHC(NH)]_nNR^cR^c$ or —$[NR^aC(NR^a)]_nNR^cR^c$;

each n, independently is an integer from 0 to 3; and each $R^d$, independently is a protecting group or $R^a$;

or a pharmaceutically acceptable salt thereof.

6. The purified compound of claim 5, wherein $P_1$ and $P_2$ are both hydrogen atoms.

7. The purified compound of claim 5, wherein Z is —C(O)$NR^cR^c$—OH.

8. The purified compound of claim 7, wherein one $R^c$ is H and the second $R^c$ is ethyl.

9. The compound of claim 1, wherein the hydrogen atom on one or more hydroxyl containing carbon atoms is substituted with an alkyl group.

10. The purified compound of claim 5, wherein the hydrogen atom on one or more hydroxyl containing carbon atoms is substituted with an alkyl group.

11. The compound of claim 1, wherein the alkyl group is a methyl group.

12. The purified compound of claim 5, wherein the alkyl group is a methyl group.

13. The compound of claim 1, further comprising a pharmaceutically acceptable carrier.

14. The compound of claim 5, further comprising a pharmaceutically acceptable carrier.

15. A method to treat inflammation, neurodegeneration, memory loss, neuroinflammation, reperfusion injury or traumatic brain injury comprising the step of administering to an individual in need thereof, an effective amount of the compound of claim 1.

16. A method to treat inflammation, neurodegeneration, memory loss, neuroinflammation, reperfusion injury or traumatic brain injury comprising the step of administering to an individual in need thereof, an effective amount of the compound of claim 5.

17. A method to treat neural development, fetal development, homeostasis, tissue remodeling, or wound repair comprising the step of administering to an individual in need thereof, an effective amount of the compound of claim 1.

18. A method to treat neural development, fetal development, homeostasis, tissue remodeling, or wound repair comprising the step of administering to an individual in need thereof, an effective amount of the compound of claim 5.

* * * * *